US008198021B2

(12) United States Patent
Ebright

(10) Patent No.: US 8,198,021 B2
(45) Date of Patent: Jun. 12, 2012

(54) TARGET AND METHOD FOR INHIBITION OF BACTERIAL RNA POLYMERASE

(75) Inventor: Richard H. Ebright, North Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 538 days.

(21) Appl. No.: 12/257,801

(22) Filed: Oct. 24, 2008

(65) Prior Publication Data

US 2010/0047780 A1 Feb. 25, 2010

Related U.S. Application Data

(63) Continuation of application No. 10/526,323, filed as application No. PCT/US03/27457 on Sep. 4, 2003, now abandoned.

(60) Provisional application No. 60/407,684, filed on Sep. 4, 2002, provisional application No. 60/474,607, filed on Jun. 2, 2003, provisional application No. 60/474,608, filed on Jun. 2, 2003.

(51) Int. Cl.
*C12Q 1/70* (2006.01)
*G01N 33/53* (2006.01)
(52) U.S. Cl. ................ 435/5; 435/7.9; 435/34
(58) Field of Classification Search .............. None
See application file for complete search history.

(56) References Cited

U.S. PATENT DOCUMENTS 6,162,613 A 12/2000 Su et al.
2002/0034808 A1* 3/2002 Darst et al. ............. 435/199

OTHER PUBLICATIONS

Korzheva N, Mustaev A, Kozlov M, Malhotra A, Nikiforov V, Goldfarb A, Darst SA, "A structural Model of Transcirption Elongation," Science, Jul. 28, 2000, 289: 619-625.*
Woychik NA, Hampsey M, "The RNA Polymerase II Machinery: Structure Illuminates Function," Cell, Feb. 22, 2002, 108: 453-463.*
Binder, S., et al., "Emerging Infectious Diseases: Public Health Issues for the 21st Century", Science, 284, 1311-1313, (May 21, 1999).
Blond, A., et al., "The cyclic structure of microcin J25, a 21-residue peptide antibiotic from *Escherichia coli*", Eur. J. Biochem., 259, 747-755, (1999).
Blondelle, S.E., et al., "Identification of Antimicrobial Peptides by using Combinatorial Libraries made up of Unnatural Amino Acids", Antimicrobial Agents and Chemotherapy, 38(10), 2280-2286, (Oct. 1994).
Blondelle, S.E., et al., "Soluble combination libraries of organic, peptidometric and peptide diversities", Trends Anal. Chem., 14, 83-92, (1995).
Bondelle, S.E., et al., "The antimicrobial activity of hexapeptides derived from synthetic combinatorial libraries", J. Appl. Bacteriol., 78(1), 39-46, (1995).
Campbell, E.A., et al., "Structural mechanism for rifampicin inhibition of bacterial RNA polymerase", Cell, 104(6), 901-912, (Mar. 23, 2001).
Cech, C. L., et al., "Characterization of ribonucleic acid polymerase-T7 promoter binary complexes", Biochemistry, 19(11), 2440-2447, (1980).
Christie, G. E., et al., "*Escherichia coli* rpoC397 Encodes a Temperature-Sensitive C-Terminal Frameshift in the beta' subunit of RNA Polymerase that Blocks Growth of Bacteriophage P2", J. Bacteriol., 178(23), 6991-6993, (Dec. 1996).
Delgado, M. A., et al., "*Escherichia coli* RNA polymerase is the target of the cyclopeptide antibiotic microcin J25", J. Bacteriol., 183(15), 4543-4550, (Aug. 2001).
Devlin, J. J., et al., "Random Peptide Libraries: A Source of Specific Protein Binding Molecules", Science, 249, 404-406, (1990).
Ebright, R. H., "RNA Polymerase: Structural Similarities between Bacterial RNA Polymerase and Eucariotic RNA Polymerase", J. Mol. Biol., 304, 687-689, (2000).
Epshtein, V., et al., "Swing-gate model of nucleotide entry into the RNA polymerase active center", Mol. Cell, 10(3), 623-634, (Sep. 2002).
Felici, F., et al., "Selection of antibody ligands from a large library of oligopeptides expressed on a multivalent exposition vector", J. Mol. Biol., 222(2), 301-310, (1991).
Gallop, M. A., et al., "Applications of Combinatorial Technologies to Drug Discovery. 1. Background and Peptide Combinatorial Libraries", J. Medicinal Chem., 37(9), 1233-1251, (Apr. 29, 1994).
Geysen, H. M., et al., "The delineation of peptides able to mimic assembled epitopes", Ciba Foundation Symposium, 119, Synthetic Peptides as Antigens, 130-149, (1986).
Gill, S. C., et al., "Calculation of protein extinction coefficients from amino acid sequence data", Analytical Biochem., 182, 319-326, (1989).
Gill, S. C., et al., "*Escherichia coli* σ70 and NusA proteins. 1. Binding interactions with core RNA polymerase in solution and within the transcription complex", J. Mol. Biol., 220, 307-324, (1991).
Gnatt, A. L., et al., "Structural Basis of Transcription: an RNA Polymerase II Elongation Complex at 3.3 A Resolution", Science, 292, 1876-1882, (Jun. 8, 2001).
Houghten, R., et al., "The use of synthetic peptide combinatorial libraries for the identification of bioactive peptides", Biotechniques, 13(3), 412-421, (Sep. 1992).
Houghten, R. A., et al., "General method for the rapid solid-phase synthesis of large numbers of peptides: Specificity of antigen-antibody interaction at the level of individual amino acids", Proc. Natl. Acad. Sci. USA, 82, 5131-5135, (Aug. 1985).
Houghten, R. A., et al., "Generation and use of synthetic peptide combinatorial libraries for basic research and drug discovery", Nature, 354(6348), 84-86, (Nov. 7, 1991).
Lam, K. S., et al., "A new type of synthetic peptide library for identifying ligand-binding activity", Nature, 54, 82-84, (1991).
Levy, S., "The Challenge of Antibiotic Resistance", Scientific American, 278(3), 46-53, (Mar. 1998).
McConnell, S. J., et al., "Constrained peptide libraries as a tool for finding mimotopes", Gene, 151(1-2), 115-118, (Dec. 30, 1994).

(Continued)

*Primary Examiner* — Julie Ha
(74) *Attorney, Agent, or Firm* — Davidson, Davidson & Kappel, LLC

(57) ABSTRACT

Target and method for inhibition of bacterial RNA polymerase disclosed are targets and methods for specific binding and inhibition of RNAP from bacterial species.

14 Claims, 7 Drawing Sheets

OTHER PUBLICATIONS

Mekler, V. A., et al., "Structural organization of bacterial RNA polymerase holoenzyme and the RNA polymerase-promoter open complex", Cell, 108(5), 599-614, (Mar. 8, 2002).

Mitchenson, D. A., "Role of individual drugs in the chemotherapy of tuberculosis", Int. J. Tuberc. Lung Disease, 4(9), 796-805, (2000).

Mukhopadhyay, J., et al., "Translocation of σ70 with RNA Polymerase during Transcription: Fluroescence Resonance Energy Transfer Assay for Movement Relative to DNA", Cell, 106, 453-463, (Aug. 24, 2001).

Murakami, K. S., et al., "Structural basis of transcription initiation: RNA polymerase holoenzyme at 4 A resolution", Science, 296(5571), 1280-1284, (May 17, 2002).

Niu, W., et al., "Transcription activation at class II CAP-dependent promoters: two interactions between CAP and RNA polymerase", Cell, 87(6), 1123-1134, (Dec. 13, 1996).

Ostresh, J. M., et al., "Libraries from librarires: Chemical transformation of combinatorial libraries to extend the range and repertoire of chemical diversity", Proc. Natl. Acad. Sci. USA, 91, 11138-11142, (Nov. 1994).

Ostresh, J. M., et al., "Peptide Libraries: Determination of Relative Reaction Rates of Protected Amino Acids in Competitive Couplings", Biopolymers, 34, 1681-1689, (1994).

Otresh, J. M., et al., "Generation and Use of Nonsupport-Bound Peptide and Peptidomimetic Combinatorial Libraries", Methods in Enzymology, Combinatorial Chemistry, vol. 267, 220-234, (1996).

Parmely, S. F., et al., "Antibody-selectable filamentous fd phage vectors: affinity purification of target genes", Gene, 73, 305-318, (1988).

Pinilla, C., et al., "A Review of the Utility of Soluble Peptide Combinatorial Libraries", Biopolymers (Peptide Science), 37, 221-240, (1995).

Pinilla, C., et al., "Rapid identification of high affinity peptide ligands using positional scanning synthetic peptide combinatorial libraries", Biotechniques, 13(6), 901-905, (Dec. 1992).

Pinilla, C., et al., Versatality of positional scanning synthetic combinatorial libraries for the identification of individual compounds:, Drug Dev. Res., 33, 133-145, (1994).

Raviglione, M. C., et al., "The Burden of Drug-Resistant Tuberculosis and Mechanisms for Its Control", Ann. NY Acad. Sci., 953, 88-97, (2001).

Schluger, N. W. et al., "The impact of drug resistance on global tuberculosis epidemic", Int. J. Tuberculosis Lung Disease, 4, S71-S75, (2000).

Scott, J. K., et al., "Searching for peptide ligands with an epitope library", Science, 249(4967), 386-390, (Jul. 27, 1990).

Solbiati, J. O., et al., "Genetic Analysis of Plasmid Determinants for Microcin J25 Production and Immunity", J. Bacteriology, 178(12), 3661-3663, (Jun. 1996).

Solbiati, J. O., et al., "Sequence Analysis of the Four Plasmid Genes Required to Produce the Circular Peptide Antibiotic Microcin J25", J. Bacteriology, 181(8), 2659-2662, (Apr. 1999).

Vassylyev, D. G., et al., "Crystal structure of a bacterial RNA polymerase holoenzyme at 2.6 A resolution", Nature, 417(6890), 712-719, (Jun. 13, 2002).

Walsh, C., "Molecular mechanisms that confer antibacterial drug resistance", Nature, 406, 775-781, (Aug. 17, 2000).

Wang, D., et al., "Discontinuous movements of DNA and RNA in RNA polymerase accompany formation of a paused transcription complex", Cell, 81(3), 341-350, (May 5, 1990).

Yuzenkova, J., et al., "Mutations of bacterial RNA polymerase leading to resistance to microcin J25", J. Biol. Chem., 277(52), 50867-50875, (Dec. 27, 2002).

Zhou, Y., et al., "Identification of the activating region of catabolite gene activator protein (CAP): Isolation and characterization of mutants of CAP specifically defective in transcription activation", Proc. Natl. Acad. Sci. USA, 90, 6081-6085, (Jul. 1993).

Zhou, Y., et al., "Random mutagenesis of gene-sized DNA molecules by use of PCR with Taq DNA polymerase", Nucl. Acids Res., 19(21), 6052, (1991).

* cited by examiner

| | | | |
|---|---|---|---|
| RPOC_ECOLI | (736) QIRQLAGMRGLM | (779) ARK | |
| RPOC_HAEIN | (737) QIRQLAGMRGLM | (780) ARK | |
| RPOC_VIBCH | (736) QIRQLAGMRGLM | (779) ARK | |
| RPOC_PSEAE | (736) QIRQLAGMRGLM | (779) ARK | |
| RPOC_TREPA | (703) QIRQLAGMRGLM | (746) ARK | |
| RPOC_BORBU | (699) QIRQLAGMRGLM | (742) ARK | |
| RPOC_XYLFA | (759) QIRQLAAMRGLM | (802) ARK | |
| RPOC_CAMJE | (734) QTSQLAAMRGLM | (777) ARK | |
| RPOC_NEIMA | (738) QIKQLSGMRGLM | (781) ARK | |
| RPOC_RICPR | (730) QIKQLGGMRGLM | (773) MRK | |
| RPOC_THEMA | (1010) QVKQLAGIRGLM | (1072) ARK | Bacterial RNA polymerase |
| RPOC_CHLTR | (736) QLKQLGALRGLM | (779) ARK | |
| RPOC_MYCPN | (820) NFTQLFGMRGLM | (874) ARK | |
| RPOC_BACSU | (740) NFTQLAGMRGLM | (783) ARK | |
| RPOC_STAAU | (744) NFTQLAGMRGLM | (787) ARK | |
| RPOC_MYCTU | (813) QTRTLAGMKGLV | (856) ARK | |
| RPOC_SYNY3 | (763) QVRQLVGMRGLM | (806) ARK | |
| RPOC_AQUAE | (850) QIRQLAGMRGLM | (893) ARK | |
| RPOC_DEIRA | (1052) QIRQLAGMRGLM | (1095) ARK | |
| RPOC_TTHER | (1034) QIRQLCGLRGLM | (1077) ARK | |
| RPOC_THEAQ | (1034) QIRQLCGMRGLM | (1077) ARK | |
| RPA1_HUMAN | (908) NTMQISCLLGQI | (971) GRE | |
| RPB1_HUMAN | (780) NISQVIAVVGQQ | (843) GRE | Human RNA polymerases I, II, and III |
| RPC1_HUMAN | (791) NISQMIACVGQQ | (854) GRE | |

FIG. 1

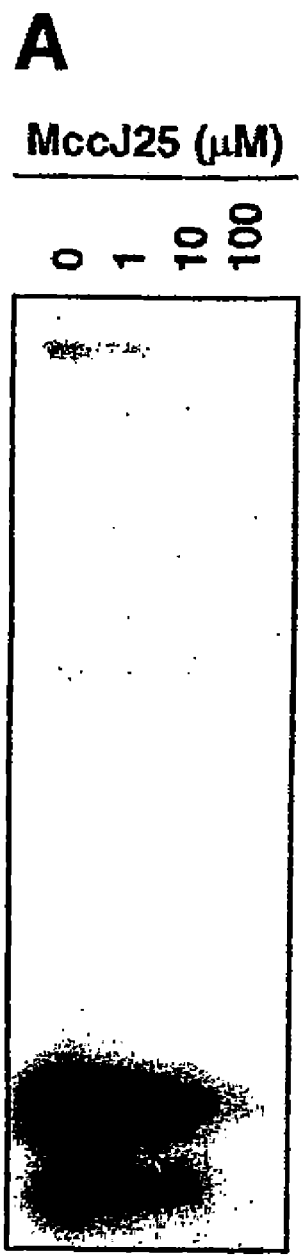 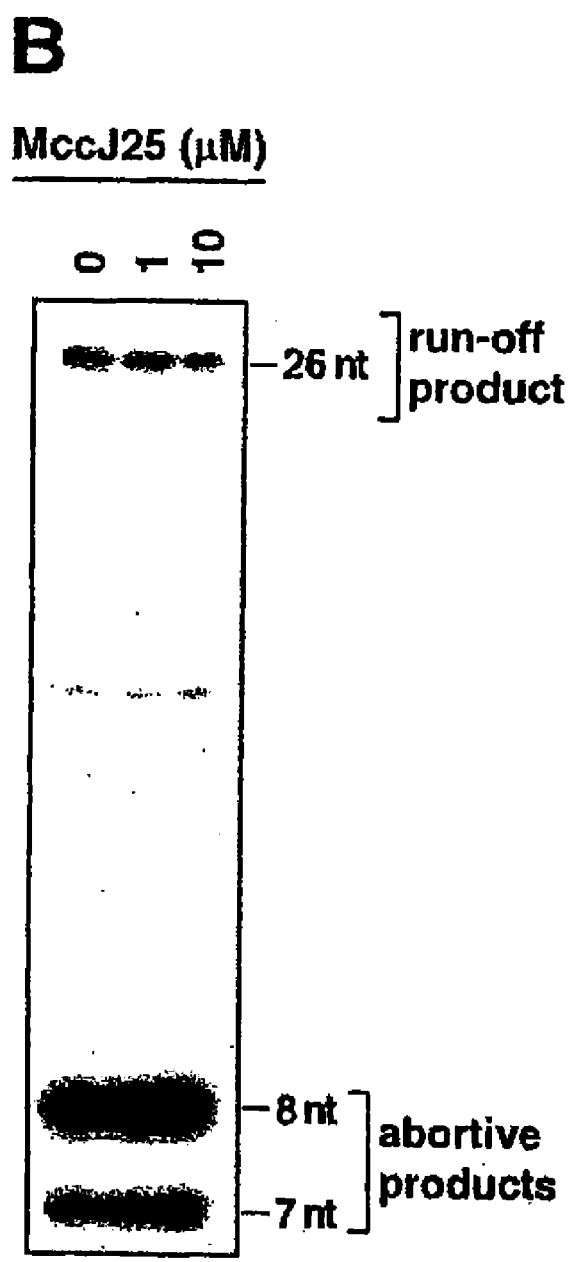
FIG. 4A  FIG. 4B

TARGET AND METHOD FOR INHIBITION OF BACTERIAL RNA POLYMERASE

CROSS-REFERENCE TO RELATED APPLICATIONS

The present application is a continuation application of U.S. application Ser. No. 10/526,323, filed on Feb. 28, 2005, which is the National Stage of International application Ser. No. PCT/US03/27457, filed on Sep. 4, 2003, which claims priority to provisional applications: 60/407,684 filed Sep. 4, 2002; 60/474,607 filed on Jun. 2, 2003; and 60/474,608 filed on Jun. 2, 2003, the entire contents of which are incorporated herein by reference.

GOVERNMENT SUPPORT

This invention was supported with U.S. Government funds (NIH RO1-GM41376). Therefore, the Government may have rights in the invention.

BACKGROUND ART

Bacterial infections remain among the most common and deadly causes of human disease. Infectious diseases are the third leading cause of death in the United States and the leading cause of death worldwide (Binder et al., Science 284:1311-1313 (1999)). Multi-drug-resistant bacteria now cause infection that poses a grave and growing threat to public health. It has been shown that bacterial pathogens can acquire resistance to first-line and even second-line antibiotics. (See, Stuart B. Levy, The Challenge of Antibiotic Resistance, in Scientific American, 46-53 (March, 1998); Walsh, C. (2000) Nature 406, 775-781; Schluger, N. (2000) Int. J. Tuberculosis Lung Disease 4, S71-S75; Raviglione et al., (2001) Ann NY Acad Sci 953, 88-97). New approaches to drug development are necessary to combat the ever-increasing number of antibiotic-resistant pathogens.

RNA is synthesized in cellular organisms by a complex molecular machine, known as RNA polymerase ("RNAP"). In its simplest bacterial form, RNAP comprises at least 4 subunits with a total molecular mass of around 400 kDa. RNAP mediates the transcription of DNA to produce RNA. Bacterial RNAP is a multimeric protein consisting of subunits $\alpha_2$, $\beta$, $\beta'$, and $\omega$. An $\sigma$ factor is required for initiation of transcription by forming a holoenzyme complex.

Currently, there are a few known antibiotics that target RNAP—notably, rifampicin and rifampicin analogs (See Mitchison, D. (2000) Int. J. Tuberculosis Lung Disease 4, 796-806). Rifampicin is the only anti-tuberculosis compound able to rapidly clear infection and prevent relapse. Without rifampicin, treatment lengths must increase from 6 months to at least 18 months to ensure prevention of relapse. Rifampicin acts by specifically inhibiting RNAP (Campbell et al., (2001) Cell 104, 901-912). Rifampicin binds to a site adjacent to the active center of bacterial RNAP, the exit channel, and physically prevents synthesis of products longer than ~4 nucleotides. Unfortunately, tuberculosis strains resistant to rifampicin (and rifampicin analogs) are becoming widespread, effectively removing rifampicin from the therapeutic arsenal. Thus, there is a need for novel antibiotics that target the same bacterial enzyme as rifampicin, RNAP, (and thus that have the same biochemical and therapeutic effects as rifampicin). There is also a need to develop methods for identifying antibiotics that interfere with bacterial RNAP.

Recently crystallographic structures have been determined for bacterial RNAP and eukaryotic RNAP II, and, based on the crystallographic structures, biophysical results, and biochemical results, models have been proposed for the structures of transcription initiation and elongation complexes (Gnatt et al.,(2001) Science 292, 1876-1882; Ebright, R. (2000) J. Mol. Biol. 304, 687-689; Naryshkin et al., (2000 Cell 101, 601-611; Kim et al., (2000) Science 288, 1418-1421; Korzheva et al., (2000) Science 289, 619-625; and Mekler et al., (2002) Cell 108:599-614). The models propose that nucleic acids completely fill the active-center cleft of RNAP, such that the only route by which incoming nucleoside triphosphate substrates (NTPs) can access the active center is through an approximately 25 Å long, 10 Å wide tunnel known as the "secondary channel" or "pore," that bores through the floor of the active-center cleft of RNAP opposite the active-center cleft. (Gnatt et al.,(2001 Science 292, 1876-1882; Ebright, R. (2000) J. Mol. Biol. 304, 687-689).

SUMMARY OF THE INVENTION

Applicant has discovered that a region within the secondary channel comprising two adjacent short peptide segments of the RNAP $\beta'$ subunit are conserved in amino-acid sequence in bacterial species, including both Gram-positive bacteria and Gram-negative bacteria. Throughout the following specification, this region is referred to as the "$\beta'$ pocket" or the "target," and the two short peptide segments are referred to as "homologous secondary channel amino acids or amino acid sequences." Applicant has also discovered that this same region is not conserved, and in fact is radically different, in amino-acid sequence in eukaryotic RNAP, such as human RNAP I, RNAP II, and RNAP III.

Accordingly, a first aspect of the present invention is directed to a method for identifying agents that bind to a homologous RNAP secondary channel amino acid sequence, comprising preparing a reaction solution comprising the agent to be tested and an entity containing a homologous secondary channel amino acid sequence; and detecting presence or amount of binding. In a preferred embodiment, detection or quantitation of binding is conducted relative to binding of the agent to an entity containing an altered homologous amino acid sequence. In other preferred embodiments, quantitation of binding is compared to binding of the 21-amino acid (GGAGHVPEYFVGOGTPISFYG) (SEQ ID NO: 1) bacteriocidal peptide microcin J25 ("MccJ25"), or a derivative thereof, to the entity via the homologous secondary channel amino acid sequence.

Another aspect of the present invention is directed to a method for identifying agents that inhibit an activity of RNAP via binding to a homologous secondary channel amino acid sequence. This aspect entails preparing a reaction solution comprising the agent to be tested, a catalytic entity containing a homologous secondary channel amino acid sequence, and a substrate for the entity; and determining extent of inhibition of RNAP activity via binding of the agent to the homologous secondary channel amino acid sequence.

In some preferred embodiments, quantitation of inhibition is compared to binding of McсJ25 to the catalytic entity via the homologous secondary channel amino acid sequence. McсJ25 is active against Gram-negative bacteria (Delgado et al., (2001) J. Bacteriol. 183:4543-4550). It was recently discovered that RNAP is a target of MccJ25. (Delgado et al., (2001) J. Bacteriol. 183:4543-4550; Yuzenkova et al., (2002) J. Biol. Chem. 277:50867-50875). The present invention provides that analogs of MccJ25 inhibit transcription by requiring determinants within the $\beta'$ pocket. The invention also provides probe-labeled derivatives of McсJ25, which can be used for detailed analysis of McсJ25 and other $\beta'$-pocketdirected inhibitors of RNAP. In one aspect of the invention, probe-labeled derivatives of MccJ25 can be used in high-throughput screening, by assessing ability of compounds or compound mixtures to compete with a probe-labeled derivative of MccJ25 for binding to RNAP or an RNAP fragment containing the target. Thus, the invention has broad applications in analysis of RNAP structure and function, control of bacterial gene expression, control of bacterial growth, antibacterial chemistry, antibacterial therapy, and drug discovery.

A further aspect of Applicants' invention is directed to an analog of MccJ25 having an amino acid sequence that differs from MccJ25 in terms of at least one amino acid deletion, insertion, or substitution, and that binds bacterial RNAP or inhibits bacterial RNAP catalytic activity to a greater extent than MccJ25.

The present invention also provides for the identification of potential antibacterial agents or antibiotics that, because of their binding affinity to regions within RNAP that are conserved among bacteria, have broad-spectrum activity. It also provides for the identification of potential anti-bacterial agents or antibiotics that, because of their substantial lack of binding affinity for eukaryotic RNAPs, will be relatively non-disruptive to normal cellular functions of the host.

It is anticipated that compounds identified according to the target and method of this invention would have applications not only in antibacterial therapy, but also in: (a) identification of bacterial RNAP (diagnostics, environmental-monitoring, and sensors applications), (b) labeling of bacterial RNAP (diagnostics, environmental-monitoring, imaging, and sensors applications), (c) immobilization of bacterial RNAP (diagnostics, environmental-monitoring, and sensors applications), (d) purification of bacterial RNA polymerase (biotechnology applications), (e) regulation of bacterial gene expression (biotechnology applications), and (f) antisepsis (antiseptics, disinfectants, and advanced-materials applications).

These and other aspects of the present invention will be better appreciated by reference to the following drawings and Detailed Description.

The file of this patent contains at least one drawing executed in color. Copies of this patent with color drawing(s) will be provided by the Patent and Trademark Office upon request and payment of the necessary fee.

BRIEF DESCRIPTION OF THE DRAWINGS

FIG. 1 illustrates a sequence alignment for the target amino acid residues 736-747 and 779-781 of the a'subunit of RNAP from *Escherichia coli* (SEQ ID NO: 2); and corresponding residues of the β'subunits of *Haemophilus influenzae* (SEQ ID NO: 3), *Vibrio cholera* (SEQ ID NO: 4), *Pseudomonas aeruginose* (SEQ ID NO: 5), *Treponema pallidum* (SEQ ID NO: 6), *Borrelia burgdorferi* (SEQ ID NO: 7), *Xyella fastidiosa* (SEQ ID NO: 8), *Camploacter jejuni* (SEQ ID NO: 9), *Neisseria meningitides* (SEQ ID NO: 10), *Rickettsia prowazekii* (SEQ ID NO: 11). *Thermotoga maritime* (SEQ ID NO: 12), *Chlamydia trachomatis* (SEQ ID NO: 13), *Mycoplasma pneumoniae* (SEQ ID NO: 14), *Bacillus subtilis* (SEQ ID NO: 15), *Staphylococcus aureus* (SEQ ID NO: 16), *Mycobacterium tuberculosis* (SEQ ID NO: 17), *Synechocystis sp.* (SEQ ID NO: 18), *Aquifex aeolicus* (SEQ ID NO: 19), *Deinococcus radiodurans* (SEQ ID NO: 20), *Thermus thermophilus* (SEQ ID NO: 21), and *Thermus aquaticus* (SEQ ID NO: 22) (collectively, "the homologous bacterial RNAP secondary channel amino acids"); and corresponding residues of the largest subunits of human RNAP I (SEQ ID NO: 23), RNAP II (SEQ ID NO: 24) and RNAP III (SEQ ID NO: 25)).

FIG. 4 illustrates that MccJ25 inhibits abortive initiation and elongation. (A) Results of transcription experiments assessing effects of MccJ25 on abortive initiation and elongation. (B) As (A), but with RNAP derivative bearing Thr931→Ile substitution in RNAP β' subunit (see Delgado et al., 2001).

BEST MODE OF CARRYING OUT THE INVENTION

The present invention provides methods of designing specific inhibitors of bacterial RNAP, the enzyme responsible for transcription. The present invention also provides for the design of small-molecule inhibitors (i.e., diameter <20 Å, MW≦2.1 kDa) that bind, with a $k_d$<1 µM, to a target site that is highly conserved in bacterial RNAP, but distinctly different in eukaryotic RNAP. The invention provides targets and methods for specific binding and inhibition of RNAP from bacterial species. The invention has applications in control of bacterial gene expression, control of bacterial growth, antibacterial chemistry, and antibacterial therapy.

Recently, crystallographic structures have been determined for bacterial RNAP and eukaryotic RNAP II (Zhang et al., (1999) *Cell* 98, 811-824; Cramer et al., (2000) *Science* 288, 640-649; Cramer et al., (2001) *Science* 292, 1863-1876; Gnatt et al., (2001 *Science* 292, 1876-1882; and Ebright, R. (2000) *J. Mol. Biol.* 304, 687-689), and, based on the crystallographic structures, biophysical results, and biochemical results, models have been proposed for the structures of transcription initiation and elongation complexes (Gnatt et al., (2001) *Science* 292, 1876-1882; Ebright, R. (2000) *J. Mol. Biol.* 304, 687-689; Naryshkin et al., (2000 *Cell* 101, 601-611; Kim et al., (2000) *Science* 288, 1418-1421; Korzheva et al., (2000) *Science* 289, 619-625; and Mekler et al., (2002) *Cell* 108:599-614).

The models for the transcription elongation complex imply that nucleic acids completely fill the active-center cleft of RNAP, and thus the only route by which incoming nucleoside-triphosphate substrates ("NTPs") can access the active center is through a ~25 Å long, ~10 Å wide tunnel—the "secondary channel" or "pore"—that bores through the floor of the active-center cleft of RNAP and extends to the exterior surface of RNAP opposite the active-center cleft (Gnatt et al., (2001) *Science* 292, 1876-1882; Ebright, R. (2000) *J. Mol. Biol.* 304, 687-689; and Korzheva et al., (2000) *Science* 289, 619-625).

The models for the transcription elongation complex imply that the RNAP secondary channel mediates multiple biochemical activities important for function of RNAP, including: uptake of NTPs, release of pyrophosphate product, release of abortive-RNA and edited-RNA products, interaction with RNA product during transcriptional pausing, interaction with RNA product during transcriptional arrest, interaction with RNA product during editing, and interaction with the elongation factors GreA and GreB.

It has now been found, and is disclosed herein, that physically blocking the RNAP secondary channel with a small molecule inhibits at least one of these activities. Specifically, it has now been found, and is disclosed herein, that physically blocking the RNAP secondary channel with a small molecule prevents uptake of NTPs by RNAP and thus inhibits transcription.

Figure 2:
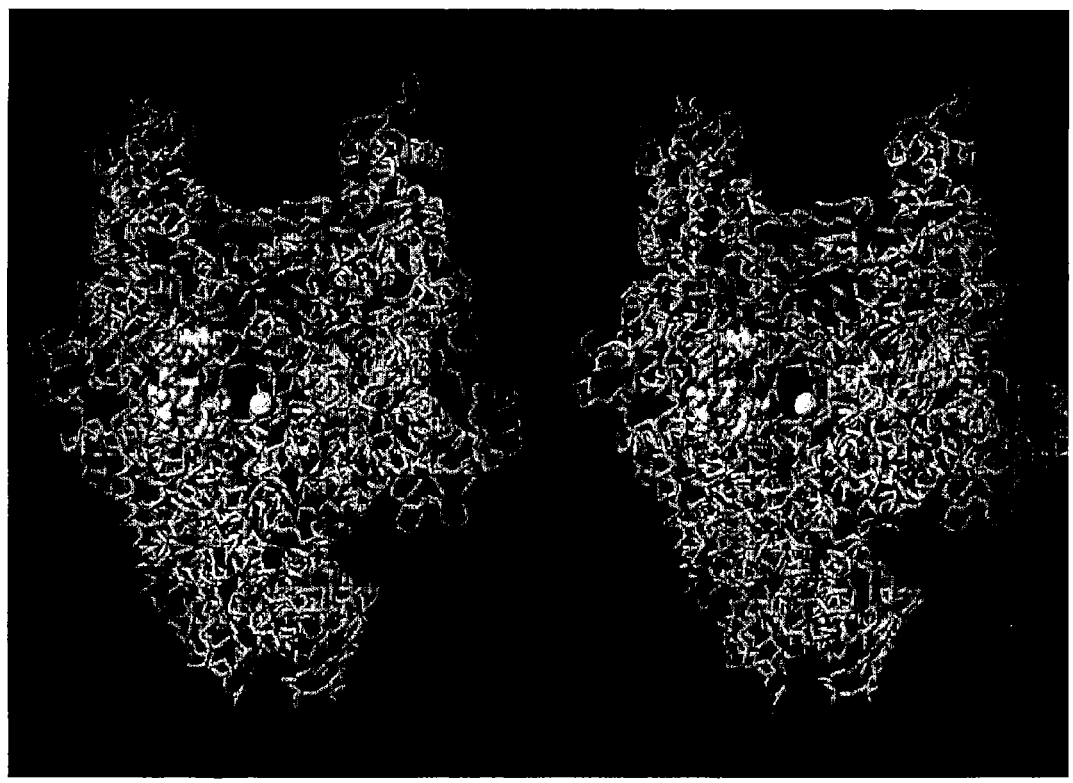
FIG. 2 illustrates a model showing the location of the target within the structure of RNAP.

The present invention is based in part on Applicant's discovery that a region within the RNAP secondary channel comprising amino acids 736-747 and 779-781 of the RNAP β' subunit from *Escherichia coli* (the "β' pocket" or "target") is a useful target for compounds that block transcription. It was found that said pocket is lined with residues that are invariant or nearly invariant in RNAP from bacterial species, but that are radically different in RNAP from eukaryotic species (FIG. 1). It further was found that this region forms a ~5 Å shallow pocket within the wall of the RNAP secondary channel (FIG. 2).

Models for the transcription elongation complex suggest that nucleic acids completely fill the active channel of RNAP, and thus that the only route by which incoming nucleoside-triphosphate (NTP) substrates can access this active center is through this secondary channel. The present invention therefore relates to molecules that bind to the secondary channel of RNAP from *Escherichia coli*, or in corresponding regions of RNAP from other bacterial species. In a preferred embodiment, the present invention relates to molecules that bind to RNAP in the secondary channel of RNAP from *Escherichia coli*, or in corresponding regions of RNAP from other bacterial species and prevent RNAP from carrying out at least one biochemical activity with which the secondary channel is associated (e.g., uptake of NTP substrates, release of pyrophosphate product, release of edited nucleotide and oligonucleotide products, interaction with RNA product during transcriptional pausing, interaction with RNA product during transcriptional arrest, interaction with RNA product during editing, and interaction with the elongation factors GreA and GreB). In one aspect of the present invention, methods and compositions are described involving compounds that specifically block the secondary channel of RNAP resulting in inhibition of transcription.

The target referred to above in *Escherichia coli* is similar in amino acid sequence to that of most or all other species of bacterial RNAP and is called herein the homologous bacterial RNAP secondary channel (FIG. 1). (For example, amino acid residues 736-747 and 779-781 of the β' subunit of RNAP from *Escherichia coli* exhibit high similarity to amino acid residues 740-751 and 783-785 of the β' subunit of RNAP from *Bacillus subtilis* (FIG. 1).) Thus, the discovery of a molecule that binds to the target and inhibits an activity associated with the secondary channel in *Escherichia coli* RNAP also is likely to bind to the target an inhibit an activity associated with the secondary channel in other species of bacterial RNAP. Therefore, molecules found to be have antibiotic activity (through binding to the target and inhibiting an activity associated with the secondary channel) against *Escherichia coli* are likely to be found to have antibiotic activity against other bacterial species.

In contrast, the target differs radically in amino acid sequence between bacterial RNAP and eukaryotic RNAP, including human RNAP I, RNAP II, and RNAP III (FIG. 1). This allows for the identification of molecules that bind, in a target-dependent fashion, to bacterial RNAP, but that do not bind, or that bind substantially less well, to eukaryotic RNAP. This also allows for the identification of molecules that inhibit, in a target-dependent fashion, an activity of to bacterial RNAP, but that do not inhibit, or that inhibit substantially less well, an activity of eukaryotic RNAP. This differentiation is important, because it permits the identification of bacterial-RNAP-selective binding molecules and bacteria-selective inhibitors.

The invention provides, by way of example only, a target region corresponding to, and alignable with residues 736-747 and 779-781 of the β' subunit of RNAP from *Escherichia coli*; as well as corresponding residues of the β' subunit of *Bacillus subtilis, Haemophilus influenzae, Vibrio cholerae, Pseudomonas aeruginosa, Treponema pallidum, Borrelia burgdorferi, Xyella fastidiosa, Campylobacter jejuni, Neisseria meningitidis, Rickettsia prowazekii, Thermotoga maritima, Chlamydia trachomatis, Mycoplasma pneumoniae, Staphylococcus aureus, Mycobacterium tuberculosis, Synechocystis* sp., *Aquifex aeolicus, Deinococcus radiodurans, Thermus thermophilus*, and *Thermus aquaticus.*

The present invention further relates to a method for identifying molecules that bind to the β' pocket through the use of an assay for molecules that bind to RNAP in a β'-pocket-specific fashion. In one embodiment, *Escherichia coli* RNAP or a fragment thereof containing the β' pocket, is used as the test protein for binding, and a derivative of said RNAP or RNAP fragment having at least one a substitution, an insertion, or a deletion within the β' pocket is used as the control protein for target-site specificity of binding. "Hits" can be analyzed for binding and inhibition of Gram-negative-bacterial RNAP, Gram-positive-bacterial RNAP, and eukaryotic RNAP I, RNAP III and RNAP III, in vivo and in vitro. "Hits"

also can be characterized structurally by x-ray diffraction analysis of co-crystals with RNAP or an RNAP fragment containing the β' pocket.

The invention also provides strategies to identify small-molecule inhibitors from compound libraries. By way of example, two strategies are described as follows: (a) selection of molecules that bind to RNAP, or a fragment thereof, in a β'-pocket-dependent fashion (affinity selection of phage-displayed linear and cyclic decapeptide libraries), and (b) screening for molecules that inhibit transcription in a β'-pocket-dependent fashion (iterative deconvolution of solution-phase linear and cyclic D-hexapeptide libraries). In each case, the invention provides the use of a wild-type bacterial RNAP, or fragment thereof, as the test protein for binding/inhibition, and a derivative of bacterial RNAP, or a fragment thereof, having at least one substitution, insertion, or deletion within the β' pocket as the control protein for β'-pocket dependence of binding/inhibition.

The invention also provides for a method of identifying a compound for use as an inhibitor of bacterial RNAP comprising: analyzing a compound or a compound library, that involves docking to, modeling of, geometric calculations with, and/or energetic calculations with, a portion of the structure of an RNAP from a bacterial species comprising at least one residue within the set of residues corresponding to, and alignable with, the target.

The invention provides for at least three drug-discovery assay methods: a) screening based on binding of a compound within the secondary channel of a bacterial RNAP or fragment thereof; b) screening based on inhibition of an activity associated with the secondary channel of a bacterial RNAP or fragment thereof; and c) screening based on displacement of a compound, containing a detectable group, from the secondary channel of a bacterial RNAP or a fragment thereof.

One of the embodiments of the present invention is an assay system designed to identify compounds that bind a bacterial RNAP, or a fragment thereof, in a manner that requires the β' pocket. The assay is designed to measure the binding of a compound to a determinant that includes at least one amino acid residue contained within a set of amino acid residues identifiable by sequence alignment and/or structure alignment as corresponding to amino acid residues 736-747 and 779-781 of Escherichia coli RNAP β' or to amino acid residues 740-751 and 783-785 of Bacillius subtilis RNAP β'.

One of the embodiments of the present invention is an assay system designed to identify compounds that inhibit an activity of a bacterial RNAP, or a fragment thereof, in a manner that requires the β' pocket. The assay is designed to measure the inhibition of an activity, said inhibition involving the binding of a compound to a determinant that includes at least one amino acid residue contained within a set of amino acid residues identifiable by sequence alignment and/or structure alignment as corresponding to amino acid residues 736-747 and 779-781 of Escherichia coli RNAP β' or to amino acid residues 740-751 and 783-785 of Bacillius subtilis RNAP β'.

Another embodiment of the present invention is an assay designed to measure the binding of a compound to a bacterial RNAP derivative, or a fragment thereof, containing at least one amino acid substitution, insertion, or deletion within a set of amino acid residues identifiable by sequence alignment and/or structure alignment as corresponding to amino acid residues 736-747 and 779-781 of Escherichia coli RNAP β' or to amino acid residues 740-751 and 783-785 of Bacillius subtilis RNAP β'.

Another embodiment of the present invention is an assay designed to measure the inhibition of an activity of a bacterial RNAP derivative, or a fragment thereof, containing at least one amino acid substitution, insertion, or deletion within a set of amino acid residues identifiable by sequence alignment and/or structure alignment as corresponding to amino acid residues 736-747 and 779-781 of Escherichia coli RNAP β' or to amino acid residues 740-751 and 783-785 of Bacillius subtilis RNAP β'.

Isolation of RNAP:

The bacterial RNAP, or RNAP derivative, can be isolated from bacteria, produced by recombinant methods, or produced through in vitro protein synthesis. Various compounds can be introduced to determine whether a tested compound binds to, inhibits an activity of, or displaces a detectable-group containing molecule from, the bacterial RNAP or RNAP derivative in a β'-pocket-dependent manner.

Tested compounds can include antibodies, peptides, and various chemical compounds. Additionally, with the known amino acid sequence for a particular RNAP, one of skill in the art could design specific inhibitors. The tested compounds can be chosen from chemical libraries, or a computer model can be used to choose compounds that are likely to be effective based on the known structure of the secondary channel, the β' pocket, and the structure of the compound.

The assay system can be performed in vivo or in vitro and thus does not necessarily require isolation of the RNAP.

The compounds can also be tested for competitive inhibition. Preferred strategies for identifying inhibitors include: 1) through affinity selection of phage-displayed linear and cyclic decapeptide libraries and 2) through iterative deconvolution of solution-phase linear and cyclic D-hexapeptide libraries. Wild type E. coli RNAP is the preferred test protein for binding and inhibition and [Val744;Gln746]β'-RNAP (a derivative of E. coli RNAP having substitutions at two positions in the β' (738-747) pocket) as the control protein. Deconvolution essentially entails the resynthesis of that combinatorial pool or mixture that was found to be active in screening against a target of interest. Resynthesis may result in the generation of a set of smaller pools or mixtures, or a set of individual compounds. Rescreening and iterative deconvolution are performed until the individual compounds that are responsible for the activity observed in the screens of the parent mixtures are isolated.

Phage Display-General Method: Searching for Peptide Ligands with an Epitope Library:

Tens of millions of short peptides can be easily surveyed for tight binding to an antibody, receptor or other binding protein using an "epitope library." (See (1990) Science 249: 386; (1990) Science 249:404; and (1990) Proc. Natl. Acad. Sci. 87:6378). The library is a vast mixture of filamentous phage clones, each displaying one peptide sequence on the virion surface. The survey is accomplished by using the binding protein to affinity-purify phage that display tight-binding peptides and propagating the purified phage in Escherichia coli. The amino acid sequences of the peptides displayed on the phage are then determined by sequencing the corresponding coding region in the viral DNA's. Potential applications of the epitope library include investigation of the specificity of antibodies and discovery of mimetic drug candidates.

"Fusion phage" are filamentous bacteriophage vectors in which foreign antigenic determinants are cloned into phage gene III and displayed as part of the gene III protein (pIII) at one tip of the virion. Fusion phage whose displayed determinant binds an antibody (Ab) can be selected from a vast background of nonbinding phage by affinity purification (AP) as follows: First, phage are reacted with biotinylated Ab (bio-Ab), then diluted and placed on a streptavidin-coated petri dish, thereby specifically attaching Ab-reactive phage to the plastic surface through the Ab-biotin-streptavidin bridge. Free phage are washed away, and bound phage eluted in acid and used to infect *Escherichia coli* cells. A single round of AP can enrich Ab-binding phage by as much as a factor of $10^5$ relative to unreactive phage; further enrichment is achieved by further rounds of AP after amplification on agar medium. Thus, Ab serves as a powerful selective agent favoring the target clones, so that vast numbers of phage can be surveyed.

The idea of using fusion phage to develop an "epitope library" (Parmley and G. P. Smith, (1988) *Gene* 73:305) was inspired by the synthetic "mimotope" strategy of Geysen et al. (See *Synthetic Peptides as Antigens; Ciba Foundation Symposium* 119, R. Porter and J. Wheelan, Eds. (Wiley, New York. 1986), pp. 131-149). By synthesizing peptide mixtures on plastic pins and assessing their ability to bind an Ab against a protein antigen, these workers delineated a peptide that mimics a discontinuous epitope—an Ab-binding determinant composed of residues distant in the primary sequence but adjacent in the folded structure. They called these peptide mimics mimotopes. In this way ligands can be discovered for an Ab whose specificity is not known in advance.

Fusion phage displaying short cloned peptides are infectious analogs of chemically synthesized mimotopes, with the key advantages of replicability and clonability. A large library of such phage—an "epitope library"—may display tens of millions of peptide epitopes. The peptides can in effect be individually surveyed for binding to an Ab or other binding protein by affinity purifying reactive phage from the library, propagating individual phage clones, and sequencing the relevant part of their DNA's to determine the amino acid sequences of their displayed peptides. A survey based on the epitope library undoubtedly would be imperfect because of bias introduced by the biology of the phage and other factors; still, it would represent a powerful new approach to the study of the specificity of Ab's and other binding proteins. (See Scott and Smith (1990) *Science* 249:386; Devlin et al., (1990) *Science* 249:404; Ciwirla et al., (1990) *Proc. Natl Acad. Sci.* 87:6378; McLafferty et al., (1993) *Gene* 128:29; Alessandra et al., (1993) *Gene* 128:51; McConnell et al., (1994) *Gene* 151:115, which are incorporated herein by reference).

Iterative Deconvolution Approach:

See the following reference for a general discussion of iterative deconvolution: (Ostresh et al., (1996) *Meths. Enzym.* 267:220, which is incorporated herein by reference). The practical development of synthetic combinatorial libraries (SCLs) made up of tens of millions of compounds has proven to be a powerful source for the identification of novel biologically active compounds such as analgesics, antibacterials, antifungals, and enzyme inhibitors. (See Pinilla et al., (1994) *Drug Dev. Res.* 33:133; Pinilla et al., (1995) *Pept. Sci.* 37:221; Gallop et al., (1994) *J. Med. Chem.* 37:1233). In particular, a range of new compounds having potent antimicrobial and/or antifungal activities have been rapidly identified from pools of millions of compounds. (See Blondelle et al., (1995) *J. Appl. Bacteriol.* 78:39; Blondelle et al., (1994) *Antimicrob. Agent Chemother.* 38:2280; Ostresh et al., (1994) *Proc. Nail. Acad. Sci. U.S.A.* 91:11138; Houghten et al., (1992) *Bio Techniques* 13:412; Houghten et al., (1991) *Nature* 354: 84).

Nonsupport-bound SCLs, originally composed of millions of peptides, were shown to be usable in virtually any assay system (including those involving membrane-bound acceptors or whole cell organisms). In an expansion of SCL concepts and diversities, the original peptide SCLs have been transformed (i.e., peralkylated and/or exhaustively reduced) using a "libraries from libraries" approach (Ostresh et al., (1994) *Proc. Nail. Acad. Sci. U.S.A.* 91:11138; Dörner et al., in "Peptides 1994: Proceedings of the 23rd European Peptide Symposium" (H. L. S. Maia, ed.), p. 463 . Escom, Leiden, 1995; and Cuervo et al., Id. at page 465) to yield peptidomimetic and organic libraries having entirely different physical, chemical, and biological properties relative to the peptide SCLs used as starting materials. The screening of such libraries has yielded active compounds derived from entirely different sequences than the active peptides previously identified from the starting SCLs using the same assay.

Two approaches can be employed for the structural deconvolution of active compounds from assay data using nonsupport-bound SCLs: the "iterative" approach and the "positional scanning" approach. In addition, two synthetic methods were developed for the incorporation of multiple functionalities at diverse positions within an SCL. As first illustrated for peptides, (See Houghten et al., (1992) *Bio Techniques* 13:412; and Houghten et al., (1991) *Nature* 354: 84, which are incorporated herein by reference). The first synthetic method, known as the "divide, couple, and recombine" (DCR) (Id.) or "split resin" (Lam et al., (1991) *Nature* 354:82) method, has typically been used with the iterative deconvolution approach. The second synthetic method, which involves the use of a predefined chemical ratio of protected amino acids at each coupling step for incorporation of mixture positions, Ostresh et al., (1994) *Biopolymers* 34:1681) has been developed for use with the positional scanning deconvolution process (Pinilla et al., (1992) *BioTechniques* 13:901). This latter method offers the advantage that both defined and mixture positions are easily incorporated at any position in a sequence.

These synthesis and deconvolution methods have been used to identify individual active compounds in a wide variety of SCLs and assays. (Pinilla et al., (1994) *Drug Dev. Res.* 33:133; Pinilla et al., (1995) *Pept. Sci.* 37:221). More specifically, individual compounds from nonsupport-bound SCLs have been identified which have potent antimicrobial activity against gram-positive bacteria (*Staphylococcus aureus, Streptococcus sanguis*), gram-negative bacteria (*Escherichia coli, Pseudomonas aeruginosa*), and fungi (*Candida albicans*). The iterative deconvolution approach will be illustrated here for the preparation of a dual-defined position hexapeptide SCL, designated OOXXXX—$NH_2$ (where O represents a defined amino acid, and X represents a mixture of amino acids) using the DCR method. The mixtures making up this library have been assayed for antimicrobial and/or antifungal activity (Blondelle et al., (1995) *Trends Anal. Chem.* 14:83; Houghten et al., (1992) *Bio Techniques* 13:412; and Houghten et al., (1991) *Nature* 354:84) in order to identify the first two amino acid residues of active hexapeptide sequences. The remaining four positions were then identified sequentially through an iterative process of synthesis and screening. This process can be completed in 6 to 10 weeks (four separate iterative synthesis steps are required). The positional scanning approach, involves the screening of separate single position SCLs to identify the most effective amino acids at each position of the sequence. When used in concert, this information can be used to identify individual active sequences. This process can be completed in approximately 2 weeks (only one synthesis step is required for confirmation of activity).

Both iterative and positional scanning peptide SCLs have been used as starting materials for the generation of peptidomimetic SCLs using the "libraries from libraries" approach.

Synthesis:

Iterative Peptide Libraries: As mentioned earlier, these libraries are prepared using the DCR process (Houghten et al., (1991) *Nature* 354:84) (in conjunction with simultaneous multiple peptide synthesis (SMPS), (Houghten, (1985) *Proc. Natl. Acad. Sci. U.S.A.* 82:5131) also known as the "tea bag"

approach. Standard t-butyloxycarbonyl (Boc)-based peptide synthesis protocols are typically used to couple protected amino acids (Bachem, Torrance, Calif.) to methylbenzhydrylamine (MBHA)-derivatized polystyrene resin (Peninsula, Belmont, Calif.). Fluorenylmethyloxycarbonyl (Fmoc)-based chemistry strategies can also be used. During preparation of the initial library, a portion of each resin mixture (i.e., X-resin, XX-resin, XXX-resin, etc) is held back for synthesis of the subsequent peptide mixtures during the iterative process in which additional positions are sequentially defined. While up to 76 amino acids have been used in the mixture positions, cysteine is normally omitted from the mixture positions of an SCL to prevent polymerization side reactions. It should be noted that for libraries synthesized by the DCR method, the number of resin beads used should be 10 to 100 times higher than the final number of individual compounds in a resin mixture in order to ensure statistical representation of each peptide in the library (Gallop et al., (1994) *I. Med. Chem.* 37:1233). The generation of a dual-defined position SCL made up of L-amino acid hexapeptides (designated OOXXXX—$NH_2$) is described here to illustrate the DCR methodology. This library contains approximately 52 million ($20^2 \times 19^4$) different peptides.

The practical use of nonsupport-bound combinatorial libraries represents an important breakthrough in all areas of basic research and drug discovery. The use of a wide variety of chemical transformations permits a range of peptidomimetic libraries to be generated, which greatly expands the chemical diversity available. The results described in this chapter demonstrate that an existing peptide PS-SCL can be chemically transformed to generate a peptidomimetic SCL from which highly active individual compounds can be identified. The synthesis and deconvolution methods developed for peptide libraries are easily applied to other types of chemical pharmacophores. The soluble nature of the nonsupport-bound combinatorial libraries is a distinct advantage over other methods in that membrane-bound and whole cell assays can also be used. In addition, the deconvolution methods used allow the chemical structure of peptidic, peptidomimetic, and organic compounds to be determined based solely on the structural similarities of compounds within each active pool or sublibrary.

Screening for an Inhibitor of Bacterial RNAP:

One aspect of the invention provides high throughput screening of molecules specific to the bacterial RNAP target. This can be done in many different ways well known in the art. For example, this could be done by attaching bacterial RNAP to the bottom of the wells of a 96-well plate at an appropriate concentration by incubating the RNAP in the well overnight at 4° C. Alternatively, the wells are first coated with compositions of polylysine that facilitates the binding of the bacterial RNAP to the wells. Following attachment, samples from a library of test compounds (concentrations are determined by the compound being tested) are added (along with an appropriate binding buffer known in the art) to the wells and incubated for a sufficient time and temperature to facilitate binding. Following the incubation, the wells are washed with an appropriate washing solution at 4° C. Increasing or decreasing salt and/or detergent concentrations in the wash varies the stringency of the washing steps. Detection of binding is accomplished using antibodies (representative examples include RIA and ELISA), biotinylation, biotin-streptavidin binding, and radioisotopes. The concentration of the sample library compounds is also varied to calculate a binding affinity by Scatchard analysis. Binding to the bacterial RNAP target identifies a "lead compound". Once a lead compound is identified, the screening process is repeated using compounds chemically related to the lead compound to identify compounds with the tightest binding affinities. Selected compounds having binding affinity are further tested in one of two assays. These assays use test compounds from 1) phage-displayed linear and cyclic decapeptide libraries and 2) iterative deconvolution of solution-phase linear and cyclic D-hexapeptide libraries.

A phage library can be used to test compounds that could bind to the β' pocket of bacterial RNAP. The phage library is constructed in the N-terminal region of the major coat protein pVIII, as previously described (Felici et al., 1991). In addition, in an attempt to define a more constrained context, two Cys are included as invariant residues flanking the random nonapeptide. Transformation yields approximately $1 \times 10^8$ independent clones, and the presence of a productive insert is indicated by the blue color of the colonies on Xgal/IPTG plates (Felici et al., 1991). The construction of the library results in hybrid capsids, expressing the random peptides, dispersed along wt pVIII copies. The absence of the Cys in wt pVIII allows one to detect the presence of free thiol groups in the hybrid capsids. Clones are analyzed with a Cys-specific recompound (DIG protein detection kit, Boehringer Mannheim, Germany) in order to show some of the peptides are in cyclized form. This indicates that in many cases the insert is displayed as a loop structure, which limits its mobility. Phage affinity purification is performed utilizing the biopanning technique, as previously described by Parmley and Smith (1988). After the round of biopanning, $10^4$ phage out of the initial $10^{10}$ are eluted from a streptavidin-coated plate. The phage are screened directly with a plaque assay. Single plagues ($10^5$) are transferred onto nitrocellulose and probed with RNAP. Positive plaques are eluted from nitrocellulose, the phage are amplified and sequenced, and their reactivity is further confirmed by dot-blot analysis. The amino acid sequences are then deduced.

Biologically active compounds are selected from large populations of randomly generated sequences. Libraries are made up of six-residue peptide sequences with amidated carboxy-termini and either acetylated or non-acetylated amino-termini. The first two amino acids in each peptide chain are individually and specifically defined, while the last four amino acids consist of equimolar, or close to equimolar, mixtures of 19 of the 20 naturally occurring L-amino acids, cysteine is omitted from the mixture positions of the two libraries but included in the defined positions. The peptides in these libraries are generally represented as Ac—$O_1O_2$XXXX—$NH_2$ and $O_1O_2$XXXX—$NH_2$, where $O_1$ and $O_2$ are defined positions, which are represented by the single letters AA, AC, AD and so on up to and including YV, YW, YY, to reach a total of 400 ($20^2$) combinations, and each X position is represented by an equimolar mixture of the 19 natural amino acids (non-natural amino acids can be used as well). Four mixture positions (XXXX) result in a total of 130,321 ($19^4$) different combinations. Each of the 400 different peptide mixtures that make up each of the libraries thus consists of 130,321 individual hexamers; in total, 52,321,400 peptides are represented. The peptides are attached to a resin or alternatively cleaved from the resin, extracted and lyophilized before use. Each nonsupport-bound peptide mixture is typically used at a concentration of 1 mg/ml. Therefore, if one assumes that the average molecular weight of Ac—$O_1O_2$XXXX—$NH_2$ is 785, then a mixture of 130,321 peptides at a total final concentration of 1 mg/ml yields a concentration of every peptide within each mixture of 7.67 ng/ml (9.8 nM), sufficiently high for most biologically significant interactions if even a single peptide sequence is active. After the mixture of libraries is screened for binding to bacterial RNAP, the remaining mixture positions are defined through an iterative enhancement and selection process in order to identify the most active sequence. An extremely rapid alternative method for identifying active compounds is the positional scanning approach. In this approach, if one uses a library made up of peptides, for example, each of the individual sub-libraries (one for each position along the peptide) that make up the positional scanning library is composed of 18 different peptide mixtures. Each position is defined (represented as O) and occupied by one of 18 of the 20 natural L-amino acids (cysteine and tryptophan are omitted); the remaining five positions of the six-residue sequence are composed of mixtures (represented as X) of the same 18 amino acids. The six different sub-libraries vary only in the location of their defined amino acids, they can therefore be represented as: Ac—$O_1$XXXXX—$NH_2$, Ac—$XO_2$XXXX—$NH_2$, Ac—$XXO_3$XXX—$NH_2$, Ac—$XXXO_4$XX—$NH_2$, AC—$XXXXO_5$X—$NH_2$, and Ac—$XXXXXO_6$—$NH_2$. As each peptide mixture represents 1,889,568 ($18^5$) individual sequences, each of the six positional sub-libraries contains in total 34,012,224 (18×1,889,568) different compounds. Alternatively, each of the six individual sub-libraries (for example, Ac—$XXXO_4$XX—$NH_2$) can be examined independently and moved forward in an interactive fashion. When used in concert, however, this set of 108 mixtures constitutes a positional scanning library.

Screening Assays for Compounds that Interfere with the Interaction of RNAP Target and MCCJ25:

The β' pocket of bacterial RNAP—which contains the target—and compounds which interact and bind are sometimes referred to herein as "binding partners." Any of a number of assay systems may be utilized to test compounds for their ability to interfere with the interaction of the binding partners. However, rapid, high-throughput assays for screening large numbers of compounds, including but not limited to ligands (natural or synthetic), peptides, or small organic molecules are preferred. Compounds that are so identified to interfere with the interaction of the binding partners should be further evaluated for binding or inhibitory activity in cell based assays, animal model systems and in patients as described herein. The basic principle of the assay systems used to identify the compounds of the present invention is based on the identification of compounds that interfere with the interaction between the target and MccJ25, which involves preparing a reaction mixture containing a bacterial RNAP, or RNAP fragment or derivative containing the secondary channel, and MccJ25 under conditions and for a time sufficient to allow the two binding partners to interact and bind, thus forming a complex. In order to test a compound for inhibitory activity, the reaction is conducted in the presence and absence of the test compound; i.e., the test compound may be initially included in the reaction mixture, or added at a time subsequent to the addition of the bacterial RNAP, or RNAP fragment or derivative containing the secondary channel, and MccJ25; controls are incubated without the test compound. The formation of a complex between the bacterial RNAP secondary channel and MccJ25 then is detected. The formation of a complex in the control reaction, but not, or to a lesser extent, in the reaction mixture containing the test compound indicates that the compound interferes with the interaction between the bacterial RNAP, or RNAP fragment or derivative containing the secondary channel, and MccJ25.

The assay components and various formats that may be utilized are described in the subsections below.

Assay Components:

The bacterial RNAP, or RNAP fragment or derivative containing the secondary channel, and MccJ25 binding partners used as components in the assay may be derived from natural sources, e.g., purified from bacterial RNAP, respectively, using protein separation techniques well known in the art; produced by recombinant DNA technology using techniques known in the art (see e.g., Sambrook et al., 1989, Molecular Cloning: A Laboratory Manual, Cold Spring Harbor Laboratories Press, Cold Spring Harbor, N.Y.); and/or chemically synthesized in whole or in part using techniques known in the art; e.g., peptides can be synthesized by solid phase techniques, cleaved from the resin and purified by preparative high performance liquid chromatography (see, e.g., Creighton, 1983, Proteins: Structures and Molecular Principles, W. H. Freeman & Co., N.Y., pp. 50-60). The composition of the synthetic peptides may be confirmed by amino acid analysis or sequencing; e.g., using the Edman degradation procedure (see e.g., Creighton, 1983, supra at pp. 34-49).

One of the binding partners used in the assay system should be labeled, either directly or indirectly, to facilitate detection of a complex formed between the bacterial RNAP secondary channel and MccJ25. Any of a variety of suitable labeling systems may be used including but not limited to radioisotopes such as $^{125}$I and $^{32}$P; enzyme labelling systems that generate a detectable colorimetric signal or light when exposed to substrate; and fluorescent labels.

Fluorescent labels are preferred. Cyanine fluorescent labels are especially preferred. Cyanine labels incorporated at residue 13 or 15 of MccJ25 are especially preferred.

Where recombinant DNA technology is used to produce the bacterial RNAP, or RNAP fragment or derivative containing the secondary channel, and MccJ25 binding partners of the assay it may be advantageous to engineer fusion proteins that can facilitate labeling, immobilization and/or detection. For example, the coding sequence of the bacterial RNAP secondary channel can be fused to that of a heterologous protein that has enzyme activity or serves as an enzyme substrate in order to facilitate labeling and detection. The fusion constructs should be designed so that the heterologous component of the fusion product does not interfere with binding of the bacterial RNAP secondary channel and MccJ25.

Indirect labeling involves the use of a third protein, such as a labeled antibody, which specifically binds to the bacterial RNAP secondary channel. Such antibodies include but are not limited to polyclonal, monoclonal, chimeric, single chain, Fab fragments and fragments produced by an Fab expression library.

For the production of antibodies, various host animals may be immunized by injection with the bacterial RNAP secondary channel. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique, which provides for the production of antibody molecules by continuous cell lines in culture. These include but are not limited to the hybridoma technique originally described by Kohler and Milstein, (Nature, 1975, 256:495-497), the human B-cell hybridoma technique (Kosbor et al., 1983, Immunology Today, 4:72, Cote et al., 1983, Proc. Natl. Acad. Sci., 80:2026-2030) and the EBV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to the bacterial RNAP secondary channel.

Antibody fragments, that recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275-1281) to allow rapid and easy identification of monoclonal Fab fragments with the desired specificity.

Assay Formats:

The assay can be conducted in a heterogeneous or homogeneous format. A heterogeneous assay is an assay in which reaction results are monitored by separating and detecting at least one component during or following reaction. A homogeneous reaction is an assay in which reaction results are monitored without separation of components. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the bacterial RNAP secondary channel and MccJ25. On the other hand, test compounds that disrupt preformed complexes, e.g. compounds with higher binding constants that displace one of the binding partners from the complex, can be tested, by adding the test compound to the reaction mixture after complexes have been formed. The various formats are described briefly below.

In one example of a heterogeneous assay system, one binding partner, e.g., either the bacterial RNAP secondary channel or MccJ25, is anchored onto a solid surface, and its binding partner, which is not anchored, is labeled, either directly or indirectly. In practice, microtiter plates are conveniently utilized. The anchored species may be immobilized by non-covalent or covalent attachments. Alternatively, an immobilized antibody specific for the bacterial RNAP secondary channel may be used to anchor the bacterial RNAP secondary channel to the solid surface. The surfaces may be prepared in advance and stored.

In order to conduct the assay, the binding partner of the immobilized species is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for an epitope on the bacterial RNAP secondary channel to anchor any complexes formed in solution. Again, depending upon the order of addition of reactants to the liquid phase, test compounds which inhibit complex or which disrupt preformed complexes can be identified.

In a preferred embodiment of the invention, a homogeneous assay can be used. In this approach, a preformed complex of the bacterial RNAP secondary channel and MccJ25 is prepared in which one of the binding partners is labeled, but the signal generated by the label is quenched due to complex formation (see, e.g., U.S. Pat. No. 4,109,496 by Rubenstein, which utilizes this approach for immunoassays). The addition of a test substance that competes with and displaces one of the binding partners from the preformed complex will result in the generation of a signal above background. In this way, test substances, which disrupt the bacterial RNAP secondary channel and MccJ25 interaction can be identified.

One aspect of the invention provides for developing methods to use fluorescence resonance energy transfer (FRET)-based homogeneous assays to provide probe-labelled derivatives of the MccJ25. (Förster, 1948; reviewed in Lilley and Wilson. 2000; Selvin, 2000; Mukhopadhyay et al., 2001; Mekler et al., 2002). FRET occurs in a system having a fluorescent probe serving as a donor and a second fluorescent probe serving as an acceptor, where the emission wavelength of the donor overlaps the excitation wavelength of the acceptor. In such a system, upon excitation of the donor with light of its excitation wavelength, energy can be transferred from the donor to the acceptor, resulting in excitation of the acceptor and omission at the acceptor's emission wavelength.

With commonly used fluorescent probes, FRET permits accurate determination of distances in the range of ~20 to ~100 Å. FRET permits accurate determination of distances up to more than one-half the diameter of a transcription complex (diameter ~150 Å; Zhang et al. 1999; Cramer et al., 2001; Gnatt et al., 2001).

A preferred assay involves monitoring of FRET between a fluorescent-probe-labeled derivative of a bacterial RNAP and a fluorescent-probe-labeled derivative of MccJ25.

An especially preferred assay involves monitoring of FRET between a coumarin-dye-labeled derivative of a bacterial RNAP and a cyanine-dye-labeled derivative of MccJ25. Especially preferred sites of labeling of RNAP for this purpose include residue 14, residue 59, or residue 517 of *Escherichia coli* RNAP $\sigma^{70}$ subunit, or a corresponding residue, identifiable by sequence and/or structural alignment, of another bacterial RNAP $\sigma$ subunit. Especially preferred sites of labeling of MccJ25 for this purpose include residue 13 and residue 15.

In accordance with the invention, a given compound found to inhibit one bacterium may be tested for general antibacterial activity against a wide range of different bacterial species. For example, and not by way of limitation, a compound that inhibits the interaction of *Escherichia coli* RNAP, or a RNAP fragment or derivative thereof containing the secondary channel, of with MccJ25 can be tested, according to the assays described infra, against *Haemophilus influenzae*.

Assays for Antibacterial Activity:

Any of the inhibitory compounds, which are identified in the foregoing assay systems, may be tested for antibacterial activity in any one of the various microbiological assays known to the skilled worker in the field of microbiology.

Animal Model Assays:

The most effective inhibitors of bacterial RNAP identified by the processes of the present invention can then be used for subsequent animal experiments. The ability of an inhibitor to prevent bacterial infection can be assayed in animal models that are natural hosts for bacteria. Such animals may include mammals such as pigs, dogs, ferrets, mice, monkeys, horses, and primates. As described in detail herein, such animal models can be used to determine the $LD_{50}$ and the $LD_{50}$ in animal subjects, and such data can be used to derive the therapeutic index for the inhibitor of the bacterial RNAP secondary channel/MccJ25 interaction.

Pharmaceutical Preparations and Methods of Administration:

The identified compounds that inhibit bacterial replication can be administered to a patient at therapeutically effective doses to treat bacterial infection. A therapeutically effective dose refers to that amount of the compound sufficient to result in amelioration of symptoms of bacterial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of infection in order to minimize damage to uninfected cells and reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection, or a half-maximal inhibition) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

As used herein a "small molecule" is a compound that has a molecular weight of less than 15 kDa.

As used herein a "small organic molecule" is an organic compound [or organic compound complexed with an inorganic compound (e.g., metal)] that has a molecular weight of less than 3 kDa.

As used herein the term "about" means within 10 to 15%, preferably within 5 to 10%. For example an amino acid sequence that contains about 60 amino acid residues can contain between 51 to 69 amino acid residues, more preferably 57 to 63 amino acid residues.

As used herein the term "target" minimally comprises amino acid residues of a target set of residues corresponding to, and alignable with, either residues 736-747 and 779-781 of the β' subunit of RNAP from *Escherichia coli* or a set of residues corresponding to, and alignable with residues 740-751 and 783-785 of the β' subunit of RNAP from *Bacillus subtilis*.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc). [Reeck et al., Cell, 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

Similarly, in a particular embodiment, two amino acid sequences are "substantially homologous" or "substantially similar" when greater than 25% of the amino acids are identical, or greater than about 50% are similar (functionally identical). Preferably, the similar or homologous sequences are identified by alignment using, for example, the GCG (Genetics Computer Group, Program Manual for the GCG Package, Version 7, Madison, Wis.) pileup program with the default parameters.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

The present invention contemplates isolation of nucleic acids encoding either targets I or I. The present invention further provides for subsequent modification of the nucleic acid to generate a fragment or modification of the target, that will crystallize.

Protein-Structure Based Design of Inhibitors of Bacterial RNAP:

Once the three-dimensional structure of a crystal comprising a bacterial RNAP target is determined, a potential modulator of the target, can be examined through the use of computer modeling using a docking program such as GRAM, DOCK, or AUTODOCK [Dunbrack et al., Folding & Design, 2:27-42 (1997)], to identify potential modulators of the bacterial RNAP target. This procedure can include computer fitting of potential modulators to the bacterial RNAP target to ascertain how well the shape and the chemical structure of the potential modulator will bind to either the individual bound subunits or to the bacterial RNAP target [Bugg et al., Scientific American, December:92-98 (1993); West et al., TIPS, 16:67-74 (1995)]. Computer programs can also be employed to estimate the attraction, repulsion, and steric hindrance of the subunits with a modulator/inhibitor (e.g., the bacterial RNAP target and a potential stabilizer).

Initially, compounds known to bind to the target—for example, MccJ25—can be systematically modified by computer modeling programs until one or more promising potential analogs are identified. In addition, systematic modification of selected analogs can then be systematically modified by computer modeling programs until one or more potential analogs are identified. Such analysis has been shown to be effective in the development of HIV protease inhibitors [Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1:109-128 (1993)]. Alternatively, a potential modulator could be obtained by initially screening a random peptide library produced by recombinant bacteriophage for example, [Scott and Smith, Science, 249:386-390 (1990); Cwirla et al., Proc. Natl. Acad. Sci., 87:6378-6382 (1990); Devlin et al., Science, 249:404-406 (1990)]. A peptide selected in this manner would then be systematically modified by computer modeling programs as described above, and then treated analogously to a structural analog as described below.

Once a potential modulator/inhibitor is identified, it can be either selected from a library of chemicals as are commercially available from most large chemical companies including Merck, Glaxo Welcome, Bristol Meyers Squib, Monsanto/Searle, Eli Lilly, Novartis and Pharmacia UpJohn, or alternatively the potential modulator may be synthesized de novo. As mentioned above, the de novo synthesis of one, or even a group of, specific compounds is reasonable in the art of drug design. The potential modulator can be placed into a standard binding assay with RNAP or an active fragment thereof such as the target, for example. The subunit fragments can be synthesized by either standard peptide synthesis described above, or generated through recombinant DNA technology or classical proteolysis. Alternatively, the corresponding full-length proteins may be used in these assays.

For example, the β' subunit can be attached to a solid support. Methods for placing the β' subunit on the solid support are well known in the art and include such things as linking biotin to the β' subunit and linking avidin to the solid support. The solid support can be washed to remove unreacted species. A solution of a labeled potential modulator (e.g., an inhibitor) can be contacted with the solid support. The solid support is washed again to remove the potential modulator not bound to the support. The amount of labeled potential modulator remaining with the solid support and thereby bound to the β' subunit can be determined. Alternatively, or in addition, the dissociation constant between the labeled potential modulator and the β' subunit, for example can be determined. Suitable labels for bacterial RNAP target or the potential modulator are exemplified herein. In a particular embodiment, isothermal calorimetry can be used to determine the stability of the bacterial RNAP target in the absence and presence of the potential modulator.

In another aspect of the present invention, a compound is assayed for its ability to bind to the target. A compound that binds to the target then can be selected. In a particular embodiment, the effect of a potential modulator on an activity of the bacterial RNAP target is determined. The potential modulator then can be added to a bacterial culture to ascertain its effect on bacterial proliferation. A potential modulator that inhibits bacterial proliferation then can be selected.

In a particular embodiment, the effect of the potential modulator on an activity of a bacterial RNAP, or a fragment thereof, is determined (either independently, or subsequent to a binding assay as exemplified above). In one such embodiment, the extent or rate of the DNA-dependent RNA transcription is determined. For such assays, a labeled nucleotide could be used. This assay can be performed using a real-time assay—e.g., with a fluorescent analog of a nucleotide. Alternatively, the determination can include the withdrawal of aliquots from the incubation mixture at defined intervals and subsequent placing of the aliquots on nitrocellulose paper or on gels. In a particular embodiment the potential modulator is selected when it is an inhibitor of the bacterial RNAP.

One assay for RNAP activity is a modification of the method of Burgess et al. [J. Biol. Chem., 244:6160 (1969)]. One unit incorporates one nanomole of UMP into acid insoluble products in 10 minutes at 37.degree. C. under the assay conditions such as those listed below. The suggested recompounds are: (a) 0.04 M Tris-HCl, pH 7.9, containing 0.01 M MgCl.sub.2, 0.15 M KCl, and 0.5 mg/ml BSA; (b) Nucleoside triphosphates (NTP): 0.15 mM each of ATP, CTP, GTP, UTP; spiked with .sup.3H-UTP 75000-150000 cpms/ 0.1 ml; (c) 0.15 mg/ml calf thymus DNA; (d) 10% cold perchloric acid; and (e) 1% cold perchloric acid. 0.1-0.5 units of RNAP in 5 .mu.1-10 .mu.1 is used as the starting enzyme concentration.

The procedure is to add 0.1 ml Tris-HCl, 0.1 ml NTP and 0.1 ml DNA to a test tube for each sample or blank. At zero time enzyme (or buffer for blank) is added to each test tube, and the contents are then mixed and incubated at 37° C. for 10 minutes. 1 ml of 10% perchloric acid is added to the tubes to stop the reaction. The acid insoluble products can be collected by vacuum filtration through MILLIPORE filter discs having a pore size of 0.45 u-10 u (or equivalent). The filters are then washed four times with 1% cold perchloric acid using 1 ml-3 ml for each wash. These filters are then placed in scintillation vials. 2 mls of methyl cellosolve are added to the scintillation vials to dissolve the filters. When the filters are completely dissolved (after about five minutes) 10 mls of scintillation fluid are added and the vials are counted in a scintillation counter.

Additional assays for analysis of RNAP activity contemplated by the present invention include RNA transcription assays and fluorescence-detected abortive initiation assays described in detail below, concerning defining the target of MccJ25. The present invention further provides for assays for analysis of antibacterial activity, such as for example include a Minimal Bacteriocidal Concentration (MBC) assay also described in detail below, concerning defining the target of MccJ25.

For calculation of units of RNAP/mg of protein the equation described in U.S. Pat. No. 6,225,076 can be used.

When suitable potential modulators are identified, a crystal can be grown that comprises the bacterial RNAP, or a fragment thereof, and the potential modulator. Preferably, the crystal effectively diffracts X-rays for the determination of the atomic coordinates of the protein-ligand complex to a resolution of better than 4.0 Angstroms. The three-dimensional structure of the crystal is determined by molecular replacement. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR (see above), CNS, (Crystallography and NMR System, a next level of XPLOR), and AMORE [J. Navaza, Acta Crystallographics ASO, 157-163 (1994)]. Once the position and orientation are known an electron density map can be calculated using the search model to provide X-ray phases. Thereafter, the electron density is inspected for structural differences and the search model is modified to conform to the new structure. Using this approach, it will be possible to solve the three-dimensional structure of different bacterial target having pre-ascertained amino acid sequences. Other computer programs that can be used to solve the structures of the bacterial RNAP from other organisms include: QUANTA, CHARMM; INSIGHT; SYBYL; MACROMODE; and ICM.

A candidate drug can be selected by performing rational drug design with the three-dimensional structure determined for the crystal, preferably in conjunction with computer modeling discussed above. The candidate drug (e.g., a potential modulator of bacterial RNAP) can then be assayed as exemplified above, or in situ. A candidate drug can be identified as a drug, for example, if it inhibits bacterial proliferation.

A potential inhibitor (e.g., a candidate antibacterial agent) would be expected to interfere with bacterial growth. Therefore, an assay that can measure bacterial growth may be used to identify a candidate antibacterial agent.

Methods of testing a potential bacteriostatic or bacteriocidal compound (e.g., the candidate antibacterial agent) in isolated cultures and in animal models are well known in the art, and can include standard minimum-inhibitory-concentration (MIC) and minimum-bacteriocidal-concentration (MBC) assays. In animal models, the potential modulators can be administered by a variety of ways including topically, orally, subcutaneously, or intraperitoneally depending on the proposed use. Generally, at least two groups of animals are used in the assay, with at least one group being a control group, which is administered the administration vehicle without the potential modulator.

For all of the assays described herein further refinements to the structure of the compound generally will be necessary and can be made by the successive iterations of any and/or all of the steps provided by the particular screening assay.

It is anticipated that compounds identified according to the target and method of this invention would have applications not only in antibacterial therapy, as described above, but also in: (i) identification of bacterial RNAP (diagnostics, environmental-monitoring, and sensors applications), (ii) labeling of bacterial RNAP (diagnostics, environmental-monitoring, imaging, and sensors applications), (iii) immobilization of bacterial RNAP (diagnostics, environmental-monitoring, and sensors applications), (iv) purification of bacterial RNA polymerase (biotechnology applications), (v) regulation of bacterial gene expression (biotechnology applications), and (vi) antisepsis (antiseptics, disinfectants, and advanced-materials applications).

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

EXAMPLES

Example 1

Cyclic Peptide MCCJ25 (MCCJ25) Inhibits Transcription by Obstructing the RNAP Secondary Channel Introduction:

The cyclic-peptide antibiotic MccJ25 (MccJ25) inhibits transcription by *Escherichia coli* RNA polymerase (RNAP) in a purified system. Biochemical results indicate that MccJ25 inhibits the abortive-initiation and elongation phases of transcription. Kinetic results indicate that MccJ25 inhibits transcription by interfering with NTP uptake. Genetic results indicate that MccJ25 inhibits transcription through interactions with an extensive determinant, comprising nearly fifty amino acid residues, within the RNAP secondary channel (also known as the secondary channel or pore). MccJ25 inhibits transcription by binding within, and obstructing, the RNAP secondary channel—acting essentially as a "cork in a bottle." Obstruction of the RNAP secondary channel represents a novel mechanism of inhibition and an attractive target for drug discovery.

MccJ25 (MccJ25) is a 21 residue cyclic-peptide antibiotic (Salomon and Farias (1992) J. Bacteriol. 174, 7428-7435; Blond et al., (1999) Eur. J. Biochem. 259, 747-755). MccJ25 is produced by *Escherichia coli* strains that harbor a plasmid-borne antibiotic-synthesis and antibiotic-export cassette, consisting of a gene for MccJ25 precursor (a 58 residue linear peptide), two genes for factors that process MccJ25 precursor into MccJ25, and one gene for export of MccJ25 (Solbiati et al., (1999) J. Bacteriol. 181, 2659-2662; Duarte et al., (2001) Can. J. Microbiol. 47, 877-882). MccJ25 exhibits bacteriocidal activity against a range of Gram-negative bacterial species, including *E. coli* (Salomon and Farias (1992) J. Bacteriol. 174, 7428-7435).

Recently, it was proposed that the functional target of MccJ25 is RNAP (RNAP). Thus, it reported that it is possible to isolate a mutant resistant to MccJ25 in rpoC—the gene for the RNAP β' subunit—and that MccJ25 inhibits RNAP-dependent transcription in crude cell extracts (Delgado et al., (2001) J. Bacteriol. 183, 4543-4550).

The present invention provides that MccJ25 inhibits transcription in a purified system, provides the steps in transcription at which inhibition occurs, provides the mechanism by which inhibition occurs, and provides define—through isolation of more than 120 independent single-substitution MccJ25-resistant mutants of rpoC following random and saturation mutagenesis—the determinant of RNAP for function of MccJ25. The present invention also provides that MccJ25 inhibits transcription by binding within, and obstructing, the RNAP secondary channel. This represents a novel mechanism for inhibition of a nucleotide polymerase and an attractive target for antibacterial drug discovery.

MCCJ25 Does Not Inhibit Open-Complex Formation:

Transcription involves the following steps (Record et al., (1996) In *Escherichia coli* and *Salmonella*, F. C. Neidhart, ed. (Washington, D.C., ASM Press), pp. 792-820; DeHaseth et al., (1998) J. Bacteriol. 180, 3019-3025): (i) RNAP binds to promoter DNA, to yield an RNAP-promoter closed complex; (ii) RNAP melts approximately 14 bp of promoter DNA surrounding the transcription start site, to yield an RNAP-promoter open complex; (iii) RNAP begins synthesis of RNA, typically carrying out multiple rounds of abortive initiation (synthesis and release of RNA products less than 9-11 nt in length), as an RNAP-promoter initial transcribing complex; and (iv), upon synthesis of an RNA product of a critical threshold length of 9-11 nt, RNAP breaks its interactions with promoter DNA and begins to translocate along DNA, processively synthesizing RNA as an RNAP-DNA elongation complex.

Figure 3:
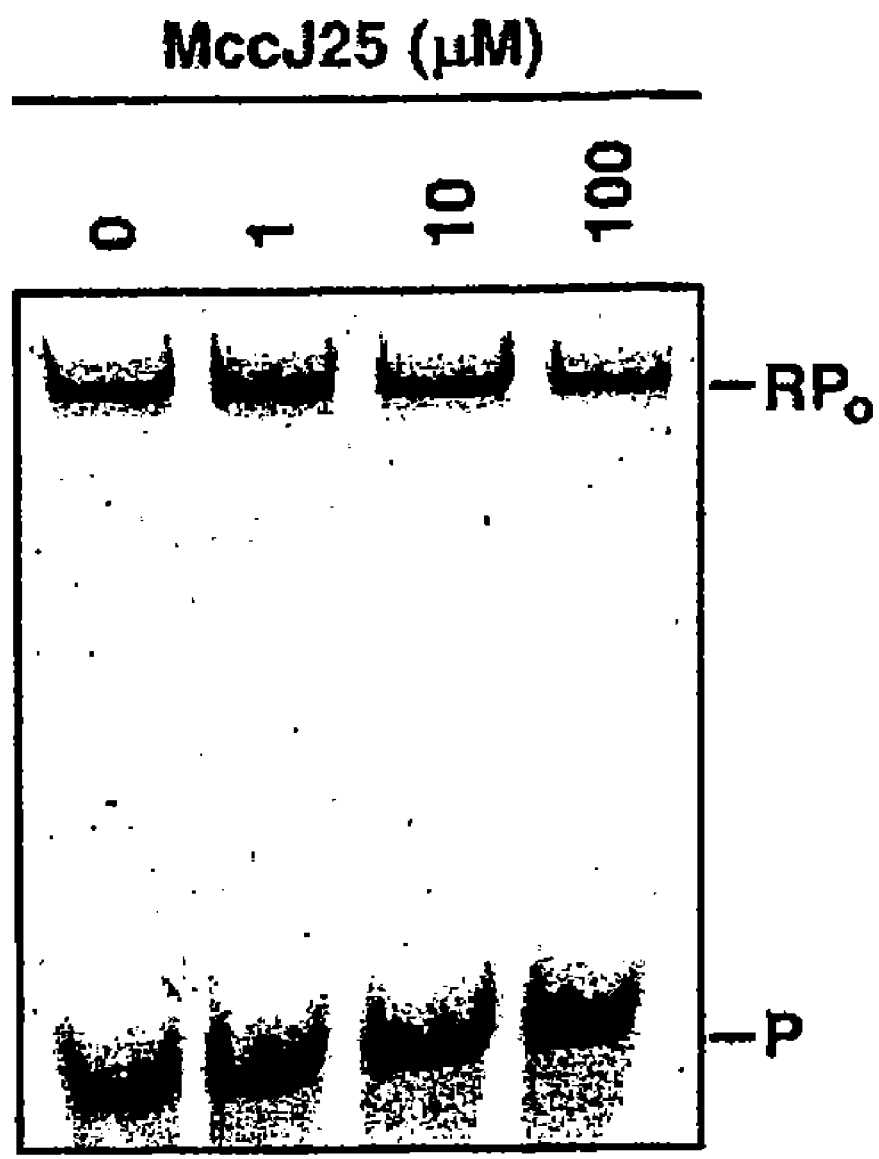
FIG. 3 illustrates that MccJ25 does not inhibit open-complex formation. Results of electrophoretic mobility shift experiments assessing effects of MccJ25 on open-complex formation. $RP_o$, RNAP-promoter open complex; P, free promoter DNA.

To determine whether MccJ25 inhibits steps in transcription up to and including formation of the RNAP-promoter open complex, electrophoretic mobility-shift experiments were performed. RNAP holoenzyme was incubated with a fluorochrome-labelled DNA fragment containing the lacUV5 promoter—in parallel in the absence and presence of MccJ25—and we analyzed products by non-denaturing PAGE followed by x/y fluorescence scanning (FIG. 3). The results indicate that MccJ25 at a concentration of 1, 10, or 100 µM has no effect on formation of open complex (FIG. 3). MccJ25 does not inhibit steps in transcription up to and including formation of open complex.

MccJ25 Inhibits Abortive Initiation and Elongation:

To determine whether MccJ25 inhibits steps in transcription subsequent to formation of the RNAP-promoter open complex, standard transcription experiments were performed. RNAP holoenzyme was pre-incubated with a DNA fragment containing the lacUVS promoter to form the RNAP-promoter open complex; radiolabelled NTPs were added and RNA synthesis was allowed to proceed for 5 min at 37° C.—in parallel in the absence and presence of MccJ25—and products were analyzed by urea-PAGE followed by storage-phosphor imaging (FIG. 4). The results indicate that MccJ25 at a concentration of 1, 10, or 100 µM inhibits both formation of abortive products (7 nt and 8 nt RNA species produced in large stoichiometric excess over the DNA template (see Record et al. 1996; deHaseth et al. 1998)) and formation of the full-length product (26 nt RNA species; produced in stoichiometric equivalence with DNA template) (FIG. 4A). The inhibition is specific; thus, inhibition is overcome completely upon substitution of residue 931 of the RNAP β' subunit—the substitution shown by Delgado et al., (2001) J. Bacteriol. 183, 4543-4550, to confer resistance to MccJ25 in viva (FIG. 4B). Parallel experiments starting with a stalled elongation complex, rather than with open complex, yield equivalent results with respect to inhibition of formation of full-length (unpublished results). MccJ25 inhibits both abortive initiation and elongation. MccJ25 interferes with a process common to both abortive initiation and elongation—i.e., NTP uptake, phosphodiester-bond formation, or translocation.

Figure 5A:
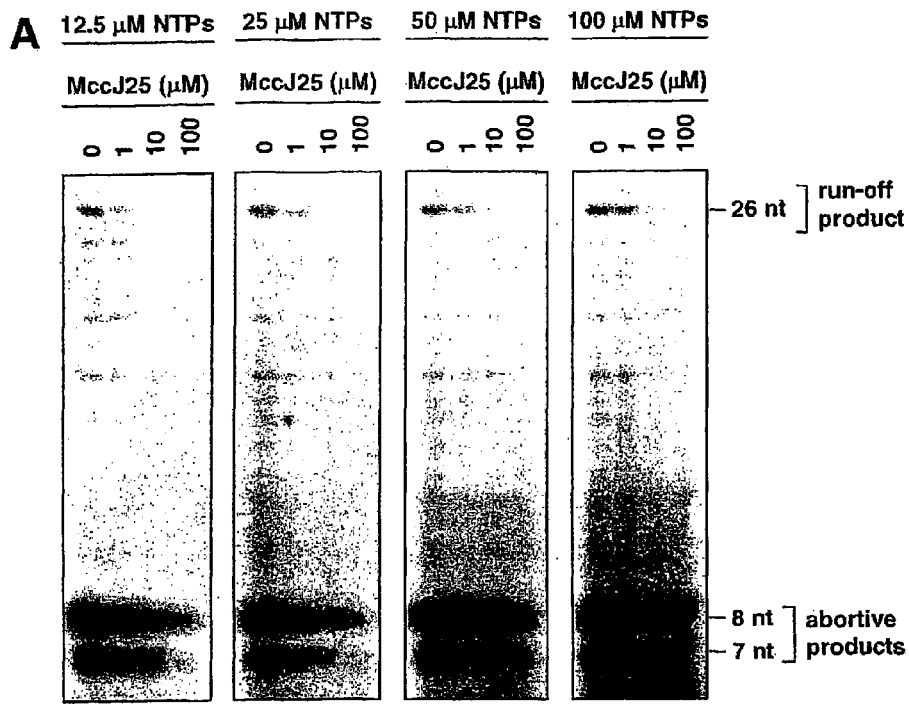
FIG. 5 illustrates that MccJ25 inhibits at the level of NTP uptake. (A) Results of transcription experiments assessing NTP-concentration-dependence of effects of MccJ25 on abortive initiation and elongation. (B) Double-reciprocal (Lineweaver-Burk) plot for inhibition of synthesis of 7-mer and 8-mer abortive products. Filled circles, no MccJ25; open circles, 1 µM MccJ25; filled triangles, 10 µM MccJ25; open triangles, 100 µM MccJ25. Data are from (A). Lines are fits to a partial-competitive model of inhibition ($K_i$=1.4±0.2 µM; α=15±3; $r^2$=0.99). (C) Double-reciprocal (Lineweaver-Burk) plot for inhibition of synthesis of 3-mer and 4-mer abortive products. Filled circles, no MccJ25; open circles, 1 µM MccJ25; filled triangles, 10 µM MccJ25; open triangles, 100 µM MccJ25. Data are from fluorescence-detected abortive initiation assays (see Experimental Procedures). Lines are fits to a partial-competitive model of inhibition ($K_i$=1.2±0.3 µM; α=8 7±2; $r^2$=0.97).

MccJ25 Inhibits by Interfering with NTP Uptake:

To assess whether inhibition by MccJ25 is NTP-concentration-dependent, transcription experiments were performed at each of four NTP concentrations (12.5 µM, 25 µM, 50 µM, and 100 µM). The results indicate that high NTP concentrations can overcome inhibition by MccJ25 (FIG. 5A). As the NTP concentration increases, the extent of inhibition by MccJ25 decreases—both at the level of abortive products and at the level of the full-length product (FIG. 5A). Thus, inhibition by MccJ25 is NTP-concentration-dependent.

Figure 5B:
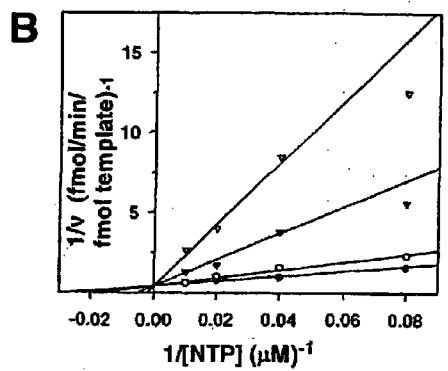
Figure 5C:
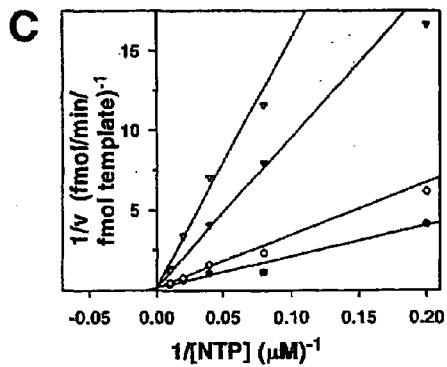

Quantitative analysis of the NTP-concentration-dependence data indicates that mode of inhibition by MccJ25 is partial competitive—i.e., that MccJ25 binds to a site on RNAP distinct from the NTP binding site and increases $K_M$ for NTPs (FIG. 5B). $K_i$, the reciprocal of the equilibrium binding constant for MccJ25-RNAP interaction, is estimated to be 1.4±0.2 µM; α, the factor by which MccJ25 increases $K_M$ for NTPs, is estimated to be 15±3 (FIG. 5B). Fluorescence-detected abortive initiation assays assessing iterative tri- and tetranucleotide synthesis—assays for which the initial-velocity assumption is rigorously valid—yield equivalent results: i.e., partial-competitive inhibition, with $K_i$=1.2±0.3 µM, and α 8.7±2 (FIG. 5C). MccJ25 inhibits transcription by binding to a site on RNAP distinct from the NTP binding site and interfering with NTP uptake.

Figure 6A:
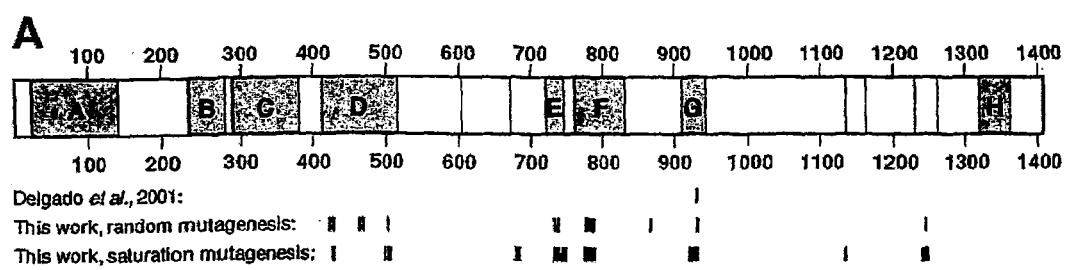
FIG. 6 illustrates that MccJ25 binds within the RNAP secondary channel. Schematic map of RNAP β' subunit showing locations of conserved regions (conserved regions A-H lettered and shaded; additional conserved regions lightly shaded) and locations of substitutions that confer MccJ25-resistance (substitution of Delgado et al., 2001 in black; substitutions from random mutagenesis as red bars; and substitutions from saturation mutagenesis in pink). (B)-(D) Three-dimensional structure of RNAP showing locations of substitutions that confer MccJ25-resistance [substitution of Delgado et al., 2001 in red in (B); substitutions from random mutagenesis in red in (C); and substitutions from random and saturation mutagenesis in red in (D)]. Each panel presents a stereodiagram. In each panel, the view is directly into the RNAP secondary channel—toward the active-center $Mg^{++}$ (white sphere at center). Atomic coordinates are based on the crystallographic structure of *Thermus thermophilus* RNAP at 2.6 Å resolution (Vassylyev et al., (2002) Nature 417, 712-719) PDB accession 1IW7; σ subunit omitted for clarity). Correspondences between residues of *E. coli* RNAP β' and *T. thermophilus* RNAP β' are based on a comprehensive sequence alignment of bacterial RNAP β' subunits, archaeal RNAP A subunits, and eukaryotic RNAP largest subunits (unpublished).
Figure 6B:
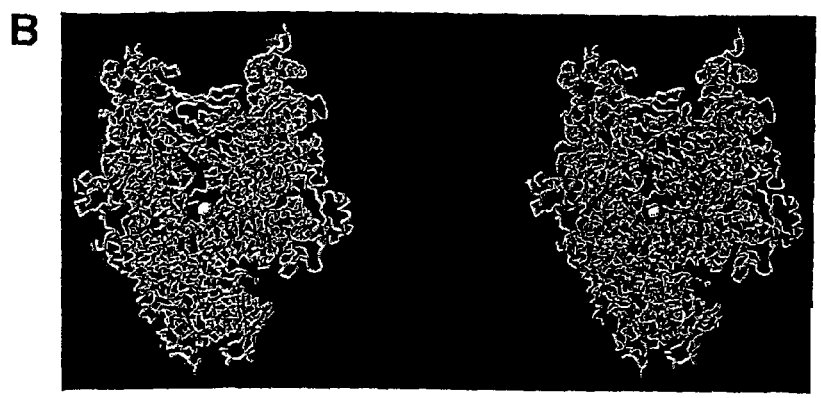

MccJ25 Binds Within the RNAP Secondary Channel—Random Mutagenesis:

The MccJ25-resistant rpoC mutant of Delgado et al. 2001 results in substitution of residue 931 of RNAP β' subunit (Thr931→Ile). In the primary structure of β', residue 931 maps to conserved region G (FIG. 6A). In the three-dimensional structure of bacterial RNAP, residue 931 of β' maps to the RNAP NTP-uptake channel (also referred to as the secondary channel or pore; FIG. 6B). The RNAP secondary channel is a 25 Å long ~10-15 Å wide, tunnel through which NTPs must pass to access the RNAP active-center and NTP binding site (Zhang et al., (1999) Cell 98, 811-824; Cramer et al., (2001) Science 292, 1863-1876; and Ebright (2000) J. Mol. Biol. 304, 687-689). The location of the substitution, in conjunction with our finding that MccJ25 inhibits transcription by interfering with NTP uptake, immediately suggests a possible mechanism of inhibition: i.e., MccJ25 may inhibit transcription by binding within, and obstructing, the RNAP secondary channel.

To define determinants of β' specifically required for transcription inhibition by MccJ25—and thereby to test the hypothesis that determinants for binding of MccJ25 are located within the RNAP secondary channel—random mutagenesis of the entire gene encoding β' were performed and isolated and characterized MccJ25-resistant mutants. (RNAP β' subunit comprises nearly one-half of all residues of RNAP and comprises all residues of the RNAP secondary channel). Mutagenesis using error-prone PCR was performed (Zhou (1991) Nucl. Acids Res. 19, 6052; Zhou et al., (1993) Proc. Natl. Acad. Sci. USA 90, 6081-6085) of five DNA segments spanning the length of a plasmid-borne rpoC gene (Table 1). Overall, 20 mutagenesis reactions were performed, ~100,000 candidates were analyzed, and 22 independent plasmid-linked MccJ25-resistant mutants were isolated (Table 1). Minimum-bacteriocidal-concentration (MBC) assays indicate that all 22 MccJ25-resistant mutants exhibit ≧50-fold increases in MBC, and 18 of 22 MccJ25-resistant mutants exhibit ≧50-fold increases in MBC (Table 2, column 5). Complementation assays indicate that all 22 MccJ25-resistant mutants can complement an rpoC$^{ts}$ mutant for growth at the non-permissive temperature, confirming that each encodes a β' derivative functional in transcription—indeed sufficiently functional in transcription to support viability (Table 2, column 4).

TABLE 1

Summary of random mutagenesis and selection codons 1-292

| | |
|---|---|
| mutagenesis reactions | 4 |
| total candidates | 11,000 |
| independent plasmid-linked MccJ25$^r$ candidates | 0 | codons 292-546

| | |
|---|---|
| mutagenesis reactions | 3 |
| total candidates | 13,000 |
| independent plasmid-linked MccJ25$^r$ candidates | 9 | codons 546-876

| | |
|---|---|
| mutagenesis reactions | 4 |
| total candidates | 11,000 |
| independent plasmid-linked MccJ25$^r$ candidates | 11 | codons 876-1213

| | |
|---|---|
| mutagenesis reactions | 5 |
| total candidates | 36,000 |
| independent plasmid-linked MccJ25$^r$ candidates | 1 | codons 1213-1408

| | |
|---|---|
| mutagenesis reactions | 4 |
| total candidates | 25,000 |
| independent plasmid-linked MccJ25$^r$ candidates | 1 | overall

| | |
|---|---|
| mutagenesis reactions | 20 |
| total candidates | 96,000 |
| independent plasmid-linked MccJ25$^r$ candidates | 22 |

For each of the 22 MccJ25-resistant mutants, the DNA-nucleotide sequence of the relevant segment of the rpoC gene was determined, and the amino acid sequence of the substituted β' derivative was inferred (Table 2). Nineteen different substitutions, involving eighteen different sites within β', were obtained (Table 2).

TABLE 2

MccJ25$^r$ isolates from random mutagenesis and selection

| | Amino acid substitution | Codon substitution | Number of independent isolates | Complementation of rpoC$^{ts}$ | MBC* (mg/ml) |
|---|---|---|---|---|---|
| | none | none | — | ++ | 0.01 |
| 424 | Asn→Ser | AAC→AGC | 1** | + | 0.1 |
| 428 | Thr→Ile | ACT→ATT | 2 | ++ | 0.5 |
| 430 | His→Leu | CAC→CTC | 3 | + | 0.5 |
| 464 | Asp→Gly | GAC→GCC | 1 | ++ | 0.05 |
| 469 | His→Arg | CAC→CGC | 1 | ++ | 0.05 |
| 504 | Gln→Arg | CAG-CGG | 1 | ++ | 0.5 |
| 733 | Ser→Phe | TCT→TTC | 1 | + | 0.5 |
| 738 | Arg→Leu | CGT→CTT | 1 | ++ | 0.05 |
| 776 | Thr→Ile | ACC→ATC | 1 | ++ | 0.5 |
| 779 | Ala→Thr | GCT→ACT | 1 | ++ | 1 |
| 780 | Arg→Cys | CGT→TGT | 1 | ++ | 1 |
| 782 | Gly→Ala | GGT→GCT | 1 | ++ | 1 |
| 785 | Asp→Gly | GAT→GGT | 1 | ++ | 0.5 |
| 786 | Thr→Ile | ACC→ATC | 1 | ++ | 0.5 |
| 789 | Lys→Arg | AAA→AGA | 1 | ++ | 0.5 |
| 789 | Lys→Gln | AAA→CAA | 1 | ++ | 1 |
| 869 | Cys→Arg | TGT→CGT | 1 | + | 1 |
| 933 | Arg→Cys | CGT→TGT | 1 | ++ | 1 |
| 1244 | Gln→Leu | CAG→CTG | 1 | ++ | 0.5 |

*Minimum bacteriocidal concentration; defined as the lowest concentration of MccJ25 that yields a viable cell count of ~0 after incubation 2 h at 37° C. (see Exeperimental Procedures).
**Isolated as double mutant 354 Val→Ile; 424 Asn→Ser; complementation and MBC data are for a single mutant constructed using site-directed mutagenesis.

Figure 6C:
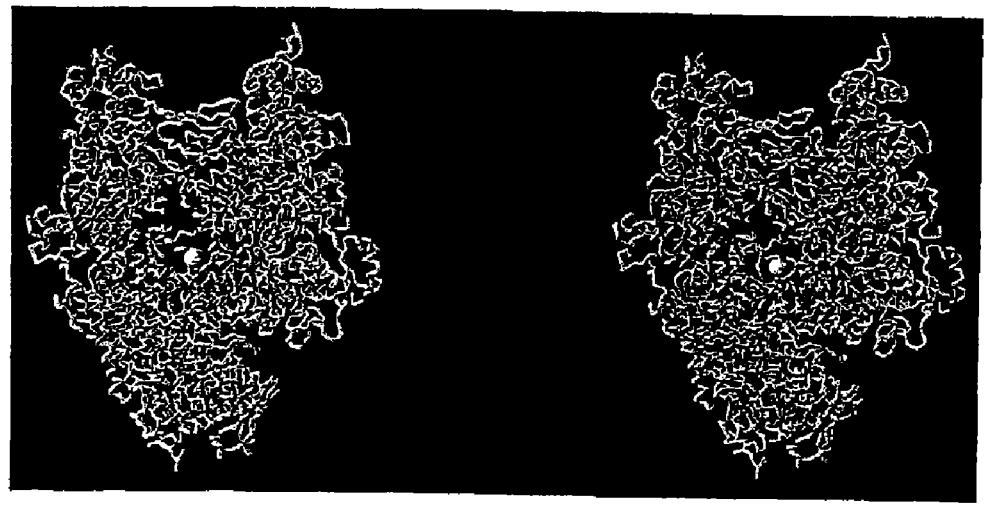

In the primary structure of β', the sites at which substitutions were obtained map to conserved region D, conserved region E, conserved region F, the segment between conserved regions F and G, conserved region G, and the segment between conserved regions G and H (referred to as conserved region G' by Zakharova et Al., (1998) J. Biol. Chem. 273, 24912-24920) (FIG. 6A). In the three-dimensional structure of RNAP, the locations of the substitutions are tightly clustered—and are centered on the RNAP secondary channel (FIG. 6C). The substitutions, without exception, map to residues that line the RNAP secondary channel, or to residues that make direct contact with residues that line the RNAP Secondary channel (FIG. 6C). The substitutions map to the floor, the roof, and the walls of RNAP secondary channel (FIG. 6C). The RNAP secondary channel contains a multi-residue determinant for function of MccJ25. Based on the fact that substitutions conferring MccJ25-resistance were obtained at none of the >1000 residues of β' outside the immediate vicinity of the secondary channel, it is concluded that no part of β' outside the immediate vicinity of the secondary channel contains a determinant for function of MccJ255.

MccJ25 Binds Within the RNAP Secondary Channel—Saturation Mutagenesis:

To define systematically the MccJ25 determinant within the RNAP secondary channel, saturation mutagenesis of the rpoC gene, was performed, targeting all codons for residues that line the RNAP secondary channel. A saturation mutagenesis using a set often "doped" oligodeoxyribonucleotide primers, designed to introduce all possible nucleotide substitutions at all positions of all codons for residues that line the RNAP secondary channel was performed (sequences in Table 3; methods essentially as in the following references (Ner et al., (1988) DNA 7, 127-134; Hermes et al., (1989) Gene 84, 143-151; and Niu et al., (1994) J. Mol. Biol. 243, 595-602). In total, 23 mutagenesis reactions were performed, ~40,000 candidates were analyzed, and 105 independent plasmid-linked MccJ25-resistant mutants were isolated and characterized (Table 4).

TABLE 3

Sequences of "doped" oligonucleotide primers used in saturation mutagenesis

| Codon | Sequence |
|---|---|
| 429-433* | CCGTGCACCGACT<u>CTGCACCGTCTGGG</u>TATCCAGGCATT TG (SEQ ID NO: 26) |
| 492-504** | GCAACAACATCCTGT<u>CCCCGGCGAACGGCGAACCAATCA TCGTTCCGTCTCAGG</u>ACGTTGTACTGGGTC (SEQ ID NO: 27) |
| 597-603* | GTCAACCAGGCGCTG<u>GGTAAAAAAGCAATCTCCAAAATG CTGAACACCTGC</u> (SEQ ID NO: 28) |
| 680-698** | CGGGCGAACGCTAC<u>AACAAAGTTATCGATATCTGGGCTG CGGCGAACGATCGTGTATCCAAAGCGATGATGGATAACC TGCAAAC</u> (SEQ ID NO: 29) |
| 726-740** | CTACATGATGGCCGACTCCGGTGCGCGTGGTTCTGCGGC ACAGATTCGTCAGCTTGCTGGTATG (SEQ ID NO: 30) |
| 741-754** | CGTCAGCTT<u>GCTGGTATGCGTGGTCTGATGGCGAAGCCG GATGGCTCCATCATCGAAACG</u> (SEQ ID NO: 31) |
| 775-790** | GTACTTCATC<u>TCCACCCACGGTGCTCGTAAAGGTCTGGC GGATACCGCACTGAAAACTGCGAACTCCG</u> SEQ ID NO: 32) |
| 922-933** | GTGTTATCGCGGGACAGT<u>CCATCGGTGAACCGGGTACAC AGCTGACCATGCGT</u>ACGTTCCACATCGGTGG (SEQ ID NO: 33) |
| 1136-1137* | CCAAGGACATCACC<u>GGTGGT</u>CTGCCGCGCGTTGC (SEQ ID NO: 34) |

TABLE 3-continued

Sequences of "doped" oligonucleotide primers used in saturation mutagenesis

| Codon | Sequence |
|---|---|
| 1239-1248** | CGAAGTACAGGACGTATACCGTGTGCAGGGCGTTAAGAT TAACGATAAAC (SEQ ID NO: 35) |

*Underlined nucleotides were synthesized using phosphoramidite reservoirs having 92% correct phosphoramidite and 8% of a 1: 1: 1: 1 mix of dA, dC, dG, and dT phosphoramidites (i.e., 94% of total correct phosphoramidites and 6% of total incorrect phosphoramidites).

**Underlined nucleotides were synthesized using phosphoramidite reservoirs having 98% correct phosphoramidite and 2% of a 1: 1: 1: 1 mix of dA, dC, dG, and dT phosphoramidites (i.e., 98.5% of total correct phosphoramidites and 1.5% of total incorrect phosphoramidites).

Sequencing indicates that 100 of the 105 MccJ25-resistant mutants are single-substitution mutants (Table 4). The single-substitution mutants comprise 71 different substitutions, involving 43 different sites within β' (Table 4).

TABLE 4

Summary of saturation mutagenesis and selection

| codons 429-433 | |
|---|---|
| mutagenesis reactions | 4 |
| total candidates | 6,000 |
| independent plasmid-linked MccJ25ʳ candidates | 8 |
| codons 492-504 | |
| mutagenesis reactions | 2 |
| total candidates | 2,000 |
| independent plasmid-linked MccJ25ʳ candidates | 9 |
| codons 597-603 | |
| mutagenesis reactions | 3 |
| total candidates | 5,000 |
| independent plasmid-linked MccJ25ʳ candidates | 0 |
| codons 680-698 | |
| mutagenesis reactions | 2 |
| total candidates | 8,000 |
| independent plasmid-linked MccJ25ʳ candidates | 6 |
| codons 726-740 | |
| mutagenesis reactions | 2 |
| total candidates | 3,000 |
| independent plasmid-linked MccJ25ʳ candidates | 12 |
| codons 741-754 | |
| mutagenesis reactions | 2 |
| total candidates | 4,000 |
| independent plasmid-linked MccJ25ʳ candidates | 5 |
| codons 775-790 | |
| mutagenesis reactions | 3 |
| total candidates | 3,000 |
| independent plasmid-linked MccJ25ʳ candidates | 33 |
| codons 922-933 | |
| mutagenesis reactions | 2 |
| total candidates | 1,000 |
| independent plasmid-linked MccJ25ʳ candidates | 13 |
| codons 1136-1137 | |
| mutagenesis reactions | 1 |
| total candidates | 2,000 |
| independent plasmid-linked MccJ25ʳ candidates | 4 |
| codons 1239-1248 | |
| mutagenesis reactions | 2 |
| total candidates | 3,000 |
| independent plasmid-linked MccJ25ʳ candidates | 15 |

TABLE 4-continued

Summary of saturation mutagenesis and selection

| overall | |
|---|---|
| mutagenesis reactions | 23 |
| total candidates | 37,000 |
| independent plasmid-linked MccJ25ʳ candidates | 105 |

Figure 6D:
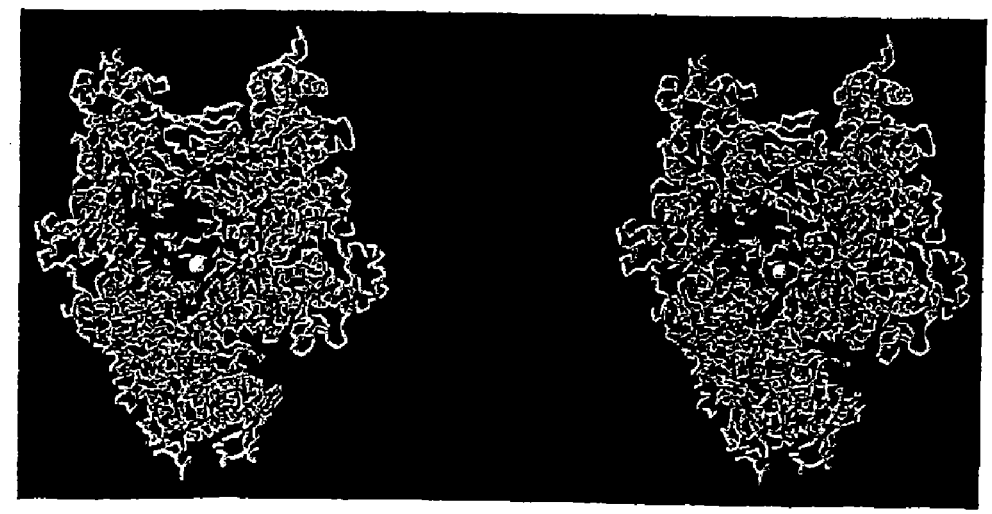

In the three-dimensional structure of RNAP, the sites at which single substitutions were obtained define a nearly continuous surface, comprising most of the interior lining and part of the rim of the RNAP secondary channel (FIG. 6D). The sites span nearly the full circumference of the RNAP secondary channel (FIG. 6D). The side chains of the majority of implicated residues are solvent-accessible—directed into the lumen of the RNAP secondary channel or toward the exterior of RNAP—and make no obvious interactions important for RNAP structure or function.

The present invention provides that the RNAP secondary channel contains an extensive determinant for function of MccJ25. Based on the size of the determinant (nearly 50 residues; Tables 3 and 6), the architecture of the determinant (interior of hollow cylinder), and the solvent-accessibility of the determinant, The present invention provides that the determinant corresponds to the binding site on RNAP for MccJ25. For reference, the size and molecular mass of MccJ25 (2,107 Da; diameter=19 Å, modeled as a sphere) would allow MccJ25 to make direct contact with all, or nearly all, residues of the determinant. The present invention also provides that the sites of substitutions that confer MccJ25-resistance map the binding site on RNAP for MccJ25 and, in essence, serve as a genetic footprint of the binding site.

TABLE 5

MccJ25ʳ isolates from saturation mutagenesis and selection

| | Amino acid substitution | Number of independent isolates | MBC* (mg/ml) |
|---|---|---|---|
| | Single-substitution mutants | | |
| 428 | Thr->Ile | 3 | 0.5 |
| 428 | Thr->Asn | 2 | 0.5 |
| 429 | Leu->Gln | 2 | 0.5 |
| 430 | His->Tyr | 1 | 0.5 |
| 498 | Pro->Leu | 1 | 1 |
| 498 | Pro->Gln | 1 | 1 |
| 503 | Ser->Pro | 1 | 0.5 |
| 503 | Ser->Tyr | 1 | 0.5 |
| 504 | Gln->Arg | 1 | 0.5 |
| 504 | Gln->Glu | 2 | 0.5 |
| 508 | Leu->Val | 1 | 0.05 |
| 680 | Asn->Lys | 2 | 0.5 |
| 684 | Asp->Ala | 1 | 1 |
| 684 | Asp->Tyr | 1 | 0.5 |
| 684 | Asp->Glu | 1 | 0.5 |
| 684 | Asp->Val | 1 | 0.5 |
| 732 | Gly->Asp | 2 | 0.1 |
| 733 | Ser->Phe | 1 | 0.1 |
| 733 | Ser->Val | 1 | 0.5 |
| 733 | Ser->Tyr | 1 | 0.1 |
| 735 | Ala->Δ | 2 | 1 |
| 736 | Gln->Pro | 1 | 0.5 |
| 738 | Arg->Leu | 1 | 0.05 |
| 744 | Arg->Pro | 1 | 0.05 |
| 744 | Arg->His | 1 | 0.05 |
| 748 | Ala->Pro | 3 | 0.1 |
| 775 | Ser->Cys | 1 | 0.5 |
| 776 | Thr->Ile | 3 | 0.5 |

TABLE 5-continued

MccJ25$^r$ isolates from saturation mutagenesis and selection

| Amino acid substitution | | Number of independent isolates | MBC* (mg/ml) |
|---|---|---|---|
| 777 | His->Tyr | 1 | 1 |
| 777 | His->Pro | 2 | 0.5 |
| 779 | Ala->Gly | 1 | 0.5 |
| 779 | Ala->Thr | 1 | 1 |
| 779 | Ala->Pro | 2 | 0.5 |
| 780 | Arg->Cys | 1 | 1 |
| 782 | Gly->Ala | 1 | 1 |
| 783 | Leu->Pro | 1 | 0.1 |
| 784 | Ala->Glu | 1 | 0.5 |
| 785 | Asp->Gly | 2 | 0.5 |
| 786 | Thr->Ile | 1 | 0.5 |
| 786 | Thr->Ala | 2 | 0.5 |
| 788 | Leu->Met | 1 | 1 |
| 789 | Lys->Asn | 2 | 1 |
| 789 | Lys->Gln | 1 | 1 |
| 789 | Lys->Arg | 1 | 0.5 |
| 790 | Thr->Ala | 2 | 1 |
| 790 | Thr->Ile | 2 | 1 |
| 790 | Thr->Ser | 2 | 0.5 |
| 790 | Thr->Asn | 1 | 0.5 |
| 922 | Cys->Tyr | 1 | 0.5 |
| 926 | Pro->Ser | 1 | 0.5 |
| 927 | Gly->Ser | 2 | 1 |
| 927 | Gly->Cys | 1 | 1 |
| 930 | Leu->Met | 1 | 1 |
| 931 | Thr->Ile | 2 | 1 |
| 931 | Thr->Ala | 2 | 1 |
| 932 | Met->Ile | 2 | 1 |
| 933 | Arg->Cys | 1 | 1 |
| 1136 | Gly->Cys | 1 | 1 |
| 1136 | Gly->Ala | 1 | 0.5 |
| 1137 | Gly->Ala | 1 | 0.5 |
| 1137 | Gly->Arg | 1 | 1 |
| 1240 | Val->Glu | 1 | 0.5 |
| 1241 | Tyr->Ser | 2 | 0.1 |
| 1241 | Tyr->His | 2 | 0.1 |
| 1241 | Tyr->Cys | 1 | 0.1 |
| 1244 | Gln->Pro | 2 | 0.1 |
| 1244 | Gln->Leu | 1 | 0.5 |
| 1244 | Gln->Glu | 2 | 0.1 |
| 1247 | Lys->Glu | 2 | 0.1 |
| 1247 | Lys->Gln | 1 | 0.1 |
| 1248 | Ile->Ser | 1 | 0.1 |
| multiple-substitution mutants | | | |
| 493 | Pro->Thr | 1 | 0.1 |
| 498 | Pro->Thr | | |
| 732 | Gly->Asp | 1 | 0.1 |
| 733 | Ser->Ala | | |
| 732 | Gly->Asp | 1 | 0.5 |
| 735 | Gly->Thr | | |
| 733 | Ser->Val | 1 | 0.1 |
| 734 | Ala->Gly | | |
| 777 | His->Ser | 1 | 0.5 |
| 778 | Gly->Ala | | |

Minimum bacteriocidal concentration; defined as the lowest concentration of MccJ25 that yields a viable cell count of ~0 after incubation 2 hr at 37° C. (see Experimental Procedures).

Thirteen of fifteen sites associated with the highest level of MccJ25-resistance (MBC=1 mg/ml; Tables 2 and 5) cluster in an ~20 Å×~20 Å×20 Å sub-region of the RNAP secondary channel, bounded by the α-helix containing residue 684 (D/E helix), the α-helix containing residue 735 (E helix), the α-helix containing residues 777-790 (F helix), the α-helix and loop containing residues 927-933 (G helix and loop), and loop containing residues 1136-1137 (G' loop) (sub-region above and to left of the active-center Mg$^{++}$ in view in FIG. 6D). The present invention provides that this sub-region is the most important part of the determinant.

Single substitutions at five sites within β' confer MccJ25-resistance: 733, 783, 931, 935, and 1138 (Yuzenkova et al., (2002) J. Biol. Chem. 277, 50867-50875). The target for MccJ25 includes these sites within β' (four of which are reported herein; Tables 2 and 5).

The present invention provides that MccJ25 inhibits the abortive-initiation and elongation phases of transcription, that inhibition involves interference with NTP uptake, that inhibition is partial-competitive with respect to NTPs (i.e., involves a site distinct from the RNAP NTP binding site), and that inhibition involves an extensive determinant within the RNAP secondary channel, comprising nearly the entire lining of the RNAP secondary channel (nearly fifty sites for substitutions conferring MccJ25-resistance). The results of Yuzenkova et al., (2002) J. Biol. Chem. 277, 50867-50875, although limited, also indicate that inhibition involves a multi-residue determinant within the RNAP secondary channel (five sites for substitutions conferring MccJ25-resistance) Preliminary results of fluorescence-resonance-energy-transfer experiments with a fluorochrome-labelled MccJ25 derivative provide direct evidence that MccJ25 binds within the RNAP secondary channel (methods as in Mekler et al., (2002) Cell 108, 599-6 14). The RNAP secondary channel is a 25 Å long, ~10-15 Å wide, fully enclosed tunnel through which NTPs must pass to access the RNAP active-center and NTP binding site (Zhang et al., (1999) Cell 98, 811-824; Cramer et al., (2001) Science 292, 1863-1876; and Ebright (2000) J. Mol. Biol. 304, 687-689). MccJ25 inhibits transcription by binding within, and obstructing, the RNAP secondary channel—acting essentially as a "cork in a bottle."

The present invention also provides that a molecule the size of MccJ25 (2.1 kDa; diameter=19 Å, modeled as a sphere) readily could bind within, and obstruct, the RNAP secondary channel (dimensions=25 Å by 10-15 Å).

Obstruction of the RNAP secondary channel represents a novel mechanism of inhibition of RNAP. Rifampicin, an inhibitor of bacterial RNAP, functions by sterically preventing synthesis of an RNA product longer than ~4 nt (Campbell et al., (2001) Cell 104, 901-912). Streptolydigin and α-amanitin, inhibitors of bacterial RNAP and eukaryotic RNAP II, respectively, are proposed to interfere with active-center conformational changes associated with phosphodiester-bond formation and/or translocation (Epshtein et al., (2002) Mol. Cell 10, 623-634; Bushnell et al., (2002) Proc. Natl. Acad. Sci. USA 99, 1218-1222).

Several arguments suggest that obstruction of the RNAP secondary channel represents an exceptionally attractive target for development of novel antimicrobial agents. First, the RNAP secondary channel is eminently "druggable," presenting an extended, encircling surface complementary to a range of molecules—like MccJ25—that have molecular weights of 500-2,500 Da. Second, the RNAP secondary channel exhibits distinct patterns of sequence conservation in bacterial RNAP and eukaryotic RNAP, permitting identification of agents—like MccJ25—that inhibit bacterial RNAP but do not inhibit eukaryotic RNAP. Third, the RNAP secondary channel is distinct from, and well-separated from, the binding site of the RNAP inhibitor in current use in antimicrobial therapy, rifampicin, permitting identification of agents—like MccJ25 (unpublished data)—that do not exhibit cross-resistance with rifampicin.

Experimental Procedures:

Plasmids:

Plasmid pTUC202 carries genes for synthesis and export of MccJ25 (Solbiati et al., (1999) J. Bacteriol. 181, 2659-2662; gift of Dr. F. Moreno). Plasmid pRL663 encodes C-terminally hexahistidine-tagged E. coli RNAP β' subunit under control of the tac promoter (Wang et al., (1995) Cell 81, 341-350; gift of Dr. R. Landick). Plasmid pREII-NHα encodes N-terminally hexahistidine-tagged E. coli RNAP α subunit under control of tandem lpp and 'lacUV5 promoters (Niu et al., 1996).

MccJ25:

MccJ25 was purified essentially as in Blond et al. 1999. E. coli strain DH5α (hsdR17 recA1 relA1 endA1 gyrA96 gal deoR phoA supE44 thi Δ(lacZYA-argF) U169ø80dlacZΔM15; Invitrogen, Inc). transformed with plasmid pTUC202 (Solbiati et al., 1996) was shaken in 1 L M9 medium (Sambrook and Russell (2001). Molecular Cloning: A Laboratory Manual (Cold Spring Harbor, N.Y., Cold Spring Harbor Laboratory)), for 24 h at 37° C., and the culture medium was harvested by centrifugation (5000×g; 15 mm at 22° C.). The culture medium was applied to a preparative C8 cartridge (10 g Mega-BE C8; Varian, Inc); the cartridge was washed successively with 50 ml water, 50 ml 20% methanol, and 50 ml 50% methanol; the cartridge was eluted with 4×5 ml fractions of 80% methanol; and fractions containing MccJ25 (detected by UV absorbance at 276 nm) were pooled, lyophilized, re-dissolved in 10 ml 20% methanol, and stored in aliquots at −20° C. Yields typically were 100 mg (determined by UV-absorbance at 276 nm using $\epsilon_{276}$=2,900 $M^{-1}$ $cm^{-1}$ (calculated as in Gill and von Hippel, 1989 (1991) J. Mol. Biol. 220, 307-324)). Purities typically were 50% (determined by analytical reversed-phase HPLC). Samples for electrophoretic mobility shift assays, transcription assays, and fluorescence-detected abortive initiation assays were further purified by reversed-phase HPLC on a C18, 5 μM, 300 Å column (Rainin, Inc)., with solvent A=20% methanol and 0.1% trifluoroacetic acid, solvent B=methanol and 0.1% trifluoroacetic acid, and gradient=0-90% solvent B in solvent A in 50 mm, flow rate=1 ml/min. Fractions containing MccJ25 (retention time ~30 mm; detected by UV absorbance at 276 nm) were pooled, lyophilized, re-dissolved in 500 μl 10% methanol, and stored in aliquots at −20° C. Yields typically were 50 mg per 1 L culture. Purities typically were >95%.

RNAP:

RNAP holoenzyme was prepared from strain XE54/pREII-NHα (the pREII-NHα; Niu et al., (1996) Cell 87, 1123-1134) using metal-ion affinity chromatography and ion-exchange chromatography (Id.). [Ile931]β'-RNAP holoenzyme was prepared from strain 397c [rpoC$^{fs}$397 argG thi lac λcI$_{857}$h$_{80}$S$_{r68}$dlac$^+$); Christie et al., (1996) J. Bacteriol. 178, 699 1-6993) transformed with a pRL663 derivative encoding [Ile931]β'-RNAP (constructed using site-directed mutagenesis (QuikChange Site-Directed Mutagenesis Kit; Stratagene, Inc).) using identical procedures. Yields typically were 6 mg. Purities typically were >95%.

Electrophoretic Mobility Shift Assays:

Reaction mixtures contained (20 μl): 100 nM RNAP holoenzyme, 20 nM DNA fragment lacUV5-12(Cy5, +26) (Mukhopadhyay et al., (2001) Cell 106, 453-463), and 0-100 μM MccJ25 in TB [50 mM Tris-HCl (pH 8.0), 100 mM KCl, 10 mM MgCl$_2$, 1 mM dithiothreitol, 10 μg/ml bovine serum albumin, and 5% glycerol]. Following 15 min at 37° C., 0.5 μl 1 mg/ml heparin was added (to disrupt non-specific complexes (Cech and McClure (1980) Biochem. 19, 2440-2447)), and, following a further 2 min at 37° C., reaction mixtures were applied to 5% polyacrylamide slab gels (30:1 acrylamide/bisacrylamide; 6×9×0.1 cm) and electrophoresed in 90 mM Tris-borate (pH 8.0) and 0.2 mM EDTA (20 V/cm; 30 min at 37° C.) and analyzed using an x/y fluorescence scanner (Storm 860; Molecular Dynamics, Inc.).

Transcription Assays:

Reaction mixtures contained (18 μl): 100 nM RNAP holoenzyme, 20 nM DNA fragment lacUV5-12(Cy5, +26) (Mukhopadhyay et al., (2001) Cell 106, 453-463), and 0-100 μM MccJ25 in TB. Following 15 min at 37° C., 0.5 μl 1 mg/ml heparin was added, and, following a further 2 min at 37° C., RNA synthesis was initiated by addition of 2 μl 5 mM ApA and 125 μM (or 250 jiM, 500 μM, and 1 mM) each of [α-$^{32}$P] UTP (0.6 Bq/fmol), ATP, CTP, GTP. Following 5 min at 37° C., reactions were terminated by addition of 10 μl 80% formamide, 10 mM EDTA, 0.04% bromophenol blue, and 0.04% xylene cyanol. Products were heated 10 min at 90° C., resolved by urea-PAGE (Sambrook and Russell (2001). Molecular Cloning: A Laboratory Manual (Cold Spring Harbor, N.Y., Cold Spring Harbor Laboratory)), and quantified using an x/y storage-phosphor scanner (Storm 860; Molecular Dynamics, Inc.). Data were fit to full-competitive, partial-competitive, full-noncompetitive, partial-noncompetitive, full-uncompetitive, partial-uncompetitive, full-mixed, and partial-mixed models of inhibition using the Fit-To-Model feature of the SigmaPlot Enzyme Kinetics Module (SPSS, Inc.).

Fluorescence-detected Abortive Initiation Assays:

Reaction mixtures contained (46.5 μl): 100 nM RNAP holoenzyme, 20 nM DNA fragment lacUV5-12 (Mukhopadhyay et al., (2001) Cell 106, 453-463), and 0-100 μM MccJ25 in TB. Following 15 min at 37° C., 0.5 μl mg/ml heparin was added, and, following a further 2 min at 37° C., 1 μl of 0.25-5 mM (y-AmNS)UTP (Molecular Probes, Inc.) was added, and reaction mixtures were transferred to sub-micro fluorometer cuvettes (Starna Cells, Inc.). Following 2 min at 37° C., RNA synthesis was initiated by addition of 2.5 μl 10 mM A$_p$A, and fluorescence emission intensity was monitored 5 min at 37° C. [excitation wavelength=360 nm and emission wavelength=500 nm; excitation and emission slit widths=4 nm; QuantaMaster QM1 spectrofluorometer (PTI, Inc).]. The quantity of UMP incorporated into RINA was determined from the quantity of (γ-AmNS)UTP consumed, which, in turn, was calculated as follows (Schlageck et al. 1979):

$$(\gamma\text{-AmNS})UTP_{consumed}=[(\gamma\text{-AmNS})UTP_0](F_t-F_0)/(12.4\times F_0)$$

where (γ-AmNS)UTP$_0$ is the quantity of (γ-AmNS)UTP at time 0, F$_0$ is the fluorescence emission intensity at time 0, and F$_t$ is the fluorescence emission intensity at time t. Data were fit to full-competitive, partial-competitive, full-noncompetitive, partial-noncompetitive, full-uncompetitive, partial-uncompetitive, full-mixed, and partial-mixed models of inhibition as in the preceding section.

Random Mutagenesis:

Random mutagenesis was performed by error-prone PCR amplification of the XbaI-SnaBI (codons 1-292), SnaBI-SphI (codons 292-546), SphI-SalI (codons 546-876), SalI-BspEI (codons 876-1213), and BspEI-XhoI (codons 1213-1408) rpoC segments of plasmid pRL663 (procedure of Zhou (1991) Nucl. Acids Res. 19, 6052; Zhou et al., (1993) Proc. Natl. Acad. Sci. USA 90, 6081-6085). The mutagenesis procedure yields all possible transition and transversion substitutions (Id. at Table 2). Mutagenized plasmid DNA was introduced by transformation into strain Stbl2 [mcrA Δ(mcrBC-hsdRMS-mrr) recA1 relA1 endA1 gyrA96 lon supE44 thi Δ(lac-proAB); Invitrogen, Inc.], transformants (−10$^4$ cells) were applied to LB-agar plates (Sambrook and Russell (2001). Molecular Cloning: A Laboratory Manual (Cold Spring Harbor, N.Y., Cold Spring Harbor Laboratory)) containing 1 μg/ml MccJ25 and 200 μg/ml ampicillin, and plates were incubated 24 h at 37° C. followed by 0-48 h at 25° C. For each MccJ25$^r$ clone (identified as a clone yielding a colony on the original selective plate and also yielding colonies when re-streaked to the same medium and incubated 16 h at 37° C.), plasmid DNA was prepared, plasmid DNA was introduced by transformation into strain DH5α [hsdR17 recA1 relA1 endA1 gyrA96 gal deoR phoA supE44 thi Δ(lacZYA-argF) U169ø80dlacZΔM15; Invitrogen, Inc.], transformants (~10$^4$ cells) were applied to LB-agar plates containing I μg/ml MccJ25 and 200 μg/ml ampicillin and, in parallel, to LB-agar plates containing 200 μg/ml ampicillin, and plates were incubated 16 h at 32° C. For each plasmid-linked MccJ25r clone (identified as a clone yielding comparable numbers of colonies on the plates with and without MccJ25), the nucleotide sequence of the mutagenized rpoC segment was determined by dideoxy nucleotide sequencing.

Saturation mutagenesis: A set of "doped" oligodeoxyribonucleotide primers corresponding to codons 425-437, 487-509, 592-608, 675-703, 723-743, 739-757, 772-793, 918-937, 1132-1141, and 1236-1251 of the rpoC gene of pRL663 was synthesized on an AB392 automated synthesizer (Applied Biosystems, Inc). using solid-phase β-cyanoethylphosphoramidite chemistry (sequences in Table 4). The level of "doping" (nucleotide misincorporation) was selected to yield an average of 0.4-1 substitution per molecule of oligodeoxyribonucleotide primer (equations in Hermes et al., 1989, 1990). Thus, the nucleotides corresponding to codons 429-433, 597-603, and 1136-1137 were synthesized using phosphoramidite reservoirs containing 92% of the correct phosphoramidite and 8% of a 1:1:1:1 mix of dA, dC, dG, and dT phosphoramidites (i.e., 94% total correct phosphoramidite and 6% total incorrect phosphoramidite); the nucleotides corresponding to codons 492-504, 680-698, 726-740, 74 1-754, 775-790, 922-933, and 123 9-1248 were synthesized using phosphoramidite reservoirs containing 98% of the correct phosphoramidite and 2% of a 1:1:1:1 mix of dA, dC, dG, and dT phosphoramidites (i.e., 98.5% total correct phosphoramidite and 1.5% total incorrect phosphoramidite); and all other nucleotides were synthesized using phosphoramidite reservoirs containing 100% of the correct phosphoramidite. Primer-extension mutagenesis reactions were performed using the QuikChange Site-Directed Mutagenesis Kit (Stratagene, Inc)., with a "doped" oligodeoxyribonucleotide primer, a complementary wild-type oligodeoxyribonucleotide primer, and pRL663 as template (primers at 75 nM; all other components at concentrations as specified by the manufacturer). Mutagenized plasmid DNA was introduced into cells, and plasmid-linked MccJ25$^r$ clones were identified and characterized, as in the preceding section.

Complementation Assays:

Strain 397c [rpoC$^{rs}$397 argG thi lac (λcI$_{857}$h$_{80}$S$_{t68}$dlac+); Christie et al., 1996] was transformed with pRL663 or a pRL663 derivative, transformants (~10$^4$ cells) were applied to LB-agar plates (Sambrook and Russell (2001). Molecular Cloning: A Laboratory Manual (Cold Spring Harbor, N.Y., Cold Spring Harbor Laboratory)) containing 1 μg/ml MccJ25 and 200 μg/ml ampicillin, plates were incubated 16 h at 37° C., and bacterial growth was scored.

Minimum Bacteriocidal Concentration (Mbc) Assays:

Strain DH5α [hsdR17 recA1 relA1 endA1 gyrA96 gal deoR phoA supE44 thi Δ(lacZYA-argF)U169 ø80dlacZΔM15; Invitrogen, Inc.] was transformed with pRL663 or a pRL663 derivative, transformants (10$^6$ cells) were incubated 2 h at 37° C. in 1 ml LB (Id.) containing 0.01, 0.05, 0.1, or 1 mg/ml MccJ25; aliquots (10 μl) were applied to LB-agar plates (Id). containing 200 μg/ml ampicillin; plates were incubated 16 h at 37° C.; and colonies were counted. The MBC was defined as the lowest concentration of MccJ25 that yielded a colony count of <5.

Example 2

Probe-Labelled Derivatives of Peptide Antibiotic MCCJ25

One aspect of the invention provides probe-labelled derivatives of the peptide antibiotic MccJ25 (MccJ25). The invention has broad applications in analysis of RNAP structure and function, control of bacterial gene expression, control of bacterial growth, antibacterial chemistry, antibacterial therapy, and drug discovery.

The present invention also provides a composition comprising a compound according to the general structural formula (I): J-Z-X, wherein J is MccJ25 or a substituted and/or truncated derivative thereof, Z is a covalent linker or is absent, and X is a detectable group. One aspect of the present invention, provides a composition comprising a compound according to the general structural formula (I) wherein X is selected from the group consisting of a fluorescent moiety, a phosphorescent moiety, a luminescent moiety, an absorbent moiety, a photosensitizer, a spin label, a radioisotope, an isotope detectable by nuclear magnetic resonance, a paramagnetic atom, a heavy atom, a hapten, a crosslinking agent, a cleavage agent, and combinations thereof. Another aspect of the present invention, provides a composition comprising formula (I) wherein X is a fluorescent moiety. Another aspect of the present invention, provides a composition comprising formula (I) wherein X is a cyanine dye. Another aspect of the present invention, provides a composition comprising formula (I) wherein X is a Cy3 . Another aspect of the present invention, provides a composition comprising formula (I) wherein X is a Cy5.

The present invention also provides a composition comprising a derivative of MccJ25 having a detectable group incorporated at position 13, according to the general structural formula (II): $[O_{13}—Z—X]J$, wherein O is an amino acid or amino acid derivative, Z is a covalent linker or is absent, and X is a detectable group. One aspect of the present invention, provides a composition according to formula) (II) wherein O is lysine; and wherein X is selected from the group consisting of a fluorescent moiety, a phosphorescent moiety, a luminescent moiety, an absorbent moiety, a photosensitizer, a spin label, a radioisotope, an isotope detectable by nuclear magnetic resonance, a paramagnetic atom, a heavy atom, a hapten, a crosslinking agent, a cleavage agent, and combinations thereof. A preferred aspect of the present invention, provides a composition according to formula (II) wherein X is a fluorescent moiety. An especially preferred aspect of the present invention, provides a composition according to formula (II) wherein X is a cyanine dye. An especially preferred aspect of the present invention provides a composition according to said formula (II) wherein X is Cy3 or Cy5.

The present invention also provides a composition comprising a derivative of MccJ25 having a detectable group incorporated at position 15, according to the general structural formula (III): $[O_{15}—Z—X]J$, wherein O is an amino acid or amino acid derivative, Z is a covalent linker or is absent, and X is a detectable group. One aspect of the present invention, provides a composition according to formula) (III) wherein O is lysine; and wherein X is selected from the group consisting of a fluorescent moiety, a phosphorescent moiety, a luminescent moiety, an absorbent moiety, a photosensitizer, a spin label, a radioisotope, an isotope detectable by nuclear magnetic resonance, a paramagnetic atom, a heavy atom, a hapten, a crosslinking agent, a cleavage agent, and combinations thereof. A preferred aspect of the present invention provides a composition according to formula (III) wherein X is a fluorescent moiety. An especially preferred aspect of the present invention provides a composition according to formula (III) wherein X is a cyanine dye. An especially preferred aspect of the present invention provides a composition according to said formula (III) wherein X is Cy3 or Cy5.

The present invention also provides a composition comprising a derivative of MccJ25 having a detectable group incorporated at position 17, according to the general structural formula (IV): $[O_{17}-Z-X]J$, wherein O is an amino acid or amino acid derivative, Z is a covalent linker or is absent, and X is a detectable group. One aspect of the present invention, provides a composition according to formula) (IV) wherein O is lysine; and wherein X is selected from the group consisting of a fluorescent moiety, a phosphorescent moiety, a luminescent moiety, an absorbent moiety, a photosensitizer, a spin label, a radioisotope, an isotope detectable by nuclear magnetic resonance, a paramagnetic atom, a heavy atom, a hapten, a crosslinking agent, a cleavage agent, and combinations thereof. A preferred aspect of the present invention, provides a composition according to formula (IV) wherein X is a fluorescent moiety. An especially preferred aspect of the present invention provides a composition according to formula (IV) wherein X is a cyanine dye. An especially preferred aspect of the present invention provides a composition according to said formula (IV) wherein X is Cy3 or Cy5.

The present invention also provides a composition comprising a compound according to any one of the general structural formulas (I), (II), (III), or (IV) for a) analysis, synthesis, screening, or design of ligands of RNAP; b) analysis, synthesis, screening, or design of modulators of RNAP activity; c) analysis, synthesis, screening, or design of modulators of bacterial gene expression; and d) analysis, synthesis, screening, or design of modulators of bacterial growth.

In a preferred embodiment, the invention provides for the use of a compound according to any one of the general structural formulas (I), (II), (III), or (IV) in an assay assessing the ability of a molecule, or set of molecules, to displace said compound from a bacterial RNAP, or a fragment thereof, or to compete with said compound for binding to a bacterial RNAP, or a fragment thereof.

In an especially preferred embodiment, the invention provides for the use of a compound according to any one of the general structural formulas (I), (II), (III), or (IV) in a homogeneous assay FRET assay measuring the ability of a molecule, or set of molecules, to displace said compound from a bacterial RNAP, or a fragment thereof, or to compete with said compound for binding to a bacterial RNAP, or a fragment thereof.

The present invention provides for the preparation of [Cy3-Lys13]MccJ25 (a compound according to structural formulas (I) and (II)) and demonstration that the compound binds to and inhibits RNAP with high potency. The present invention also provides for the preparation of [Lys13]MccJ25, [Lys15]MccJ25, and [Lys17]MccJ25 (intermediates in synthesis of compounds according to structural formulas (I)-(IV) and demonstration that the compounds bind to and inhibit RNAP with high potency.

The present invention also provides for the use of Cy3-Lys13]MccJ25 (a compound according to structural formulas (I) and (II)) in a homogeneous FRET assay measuring the ability of a molecule, or set of molecules, to displace said compound from a bacterial RNAP, or a fragment thereof, or to compete with said compound for binding to a bacterial RNAP, or a fragment thereof.

Industrial Applicability

The invention has applications in control of bacterial gene expression, control of bacterial growth, antibacterial chemistry, and antibacterial therapy.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated herein by reference.

What is claimed is:

1. A method for identifying an agent that binds to a homologous secondary channel amino acid sequence of a bacterial RNA polymerase (RNAP) in a first entity, comprising the steps of: (a) preparing a reaction solution including the agent to be tested and a first entity including a homologous secondary channel amino acid sequence of a bacterial RNAP; and (b) detecting at least one of the presence, extent, concentration-dependence, or kinetics of binding of the agent to the homologous secondary channel amino acid sequence, wherein the agent is not MccJ25.

2. The method of claim 1 wherein the first entity is an intact bacterial RNAP.

3. The method of claim 1 wherein the first entity is *Escherichia coli* RNAP or *Bacillus subtilis* RNAP.

4. The method of claim 1 further comprising comparison of: (a) the binding of the agent to the first entity; and (b) the binding of the agent to a second entity that contains a derivative of a bacterial RNAP homologous secondary channel amino acid sequence having at least one substitution, insertion, or deletion.

5. The method of claim 4 wherein the second entity is a derivative of an intact bacterial RNAP.

6. The method of claim 4 wherein the second entity is a *Escherichia coli* RNAP or *Bacillus subtilis* RNAP.

7. The method of claim 4 further comprising comparison of: (a) at least one of the presence, extent, concentration-dependence, or kinetics of binding of the agent to the first entity; and (b) at least one of the presence, extent, concentration-dependence, or kinetics of binding of the agent to a eukaryotic RNAP.

8. The method of claim 7 wherein the eukaryotic RNAP is selected from the group consisting of human RNAP and human RNAP II.

9. The method of claim 7 further comprising comparison of: (a) at least one of the presence, extent, concentration-dependence, or kinetics of binding of the agent to the first entity; and (b) at least one of the presence, extent, concentration-dependence, or kinetics of binding of MccJ25 to the first entity.

10. A method for identifying an agent that inhibits an activity of a bacterial RNAP by binding to a homologous secondary channel amino acid sequence of a bacterial RNAP, comprising: (a) preparing a reaction solution comprising the agent to be tested and a first entity containing a homologous secondary channel amino acid sequence of a bacterial RNAP; and (b) detecting the at least one of the presence, extent, concentration-dependence, or kinetics of inhibition of an activity of said first entity, wherein inhibition involves binding of the agent to the homologous secondary channel amino acid sequence, wherein the agent is not McCJ25.

11. The method of claim 10 wherein the first entity is an intact bacterial RNAP.

12. The method of claim 10 wherein the first entity is *Escherichia coli* RNAP or *Bacillus subtilis* RNAP.

13. The method of claim 10 wherein the activity is selected from the group consisting of RNA synthesis, NTP uptake, pyrophosphate release, abortive-RNA release, edited-RNA release, transcriptional pausing transcriptional arrest, and Gre-factor binding.

14. The method of claim 10 further comprising comparison of: (a) at least one of the presence, extent, concentration-dependence, or kinetics of the inhibition by the agent of an activity of the first entity; and (b) at least one of the presence, extent, concentration-dependence, or kinetics of the inhibition by the agent of an activity of a second entity that contains a derivative of a bacterial RNAP homologous secondary channel amino acid having at least one substitution, insertion, or deletion.

* * * * *

SEQUENCE LISTING

```
<160> NUMBER OF SEQ ID NOS: 35

<210> SEQ ID NO 1
<211> LENGTH: 21
<212> TYPE: PRT
<213> ORGANISM: bacteriocidal peptide microcin J25
<220> FEATURE:
<221> NAME/KEY: MISC_FEATURE
<222> LOCATION: (13)..(13)
<223> OTHER INFORMATION: Xaa denotes any amino acid

<400> SEQUENCE: 1

Gly Gly Ala Gly His Val Pro Glu Tyr Phe Val Gly Xaa Gly Thr Pro
1               5                   10                  15

Ile Ser Phe Tyr Gly
            20

<210> SEQ ID NO 2
<211> LENGTH: 15
```

-continued

```
<212> TYPE: PRT
<213> ORGANISM: Escherichia coli

<400> SEQUENCE: 2

Gln Ile Arg Gln Leu Ala Gly Met Arg Gly Leu Met Ala Arg Lys
1               5                   10                  15

<210> SEQ ID NO 3
<211> LENGTH: 15
<212> TYPE: PRT
<213> ORGANISM: Haemophilus influenzae

<400> SEQUENCE: 3

Gln Ile Arg Gln Leu Ala Gly Met Arg Gly Leu Met Ala Arg Lys
1               5                   10                  15

<210> SEQ ID NO 4
<211> LENGTH: 15
<212> TYPE: PRT
<213> ORGANISM: Vibrio cholera

<400> SEQUENCE: 4

Gln Ile Arg Gln Leu Ala Gly Met Arg Gly Leu Met Ala Arg Lys
1               5                   10                  15

<210> SEQ ID NO 5
<211> LENGTH: 15
<212> TYPE: PRT
<213> ORGANISM: Pseudomonas aeruginose

<400> SEQUENCE: 5

Gln Ile Arg Gln Leu Ala Gly Met Arg Gly Leu Met Ala Arg Lys
1               5                   10                  15

<210> SEQ ID NO 6
<211> LENGTH: 15
<212> TYPE: PRT
<213> ORGANISM: Treponema pallidum

<400> SEQUENCE: 6

Gln Ile Arg Gln Leu Ala Gly Met Arg Gly Leu Met Ala Arg Lys
1               5                   10                  15

<210> SEQ ID NO 7
<211> LENGTH: 15
<212> TYPE: PRT
<213> ORGANISM: Borrelia burgdorferi

<400> SEQUENCE: 7

Gln Ile Arg Gln Leu Ala Gly Met Arg Gly Leu Met Ala Arg Lys
1               5                   10                  15

<210> SEQ ID NO 8
<211> LENGTH: 15
<212> TYPE: PRT
<213> ORGANISM: Xyella fastidiosa

<400> SEQUENCE: 8

Gln Ile Arg Gln Leu Ala Ala Met Arg Gly Leu Met Ala Arg Lys
1               5                   10                  15

<210> SEQ ID NO 9
<211> LENGTH: 15
<212> TYPE: PRT
<213> ORGANISM: Camploacter jejuni
```

-continued

```
<400> SEQUENCE: 9

Gln Ile Ser Gln Leu Ala Ala Met Arg Gly Leu Met Ala Arg Lys
1               5                   10                  15

<210> SEQ ID NO 10
<211> LENGTH: 15
<212> TYPE: PRT
<213> ORGANISM: Neisseria meningitides

<400> SEQUENCE: 10

Gln Ile Lys Gln Leu Ser Gly Met Arg Gly Leu Met Ala Arg Lys
1               5                   10                  15

<210> SEQ ID NO 11
<211> LENGTH: 15
<212> TYPE: PRT
<213> ORGANISM: Rickettsia prowazekii

<400> SEQUENCE: 11

Gln Ile Lys Gln Leu Gly Gly Met Arg Gly Leu Met Met Arg Lys
1               5                   10                  15

<210> SEQ ID NO 12
<211> LENGTH: 15
<212> TYPE: PRT
<213> ORGANISM: Thermotoga maritime

<400> SEQUENCE: 12

Gln Val Lys Gln Leu Ala Gly Ile Arg Gly Leu Met Ala Arg Lys
1               5                   10                  15

<210> SEQ ID NO 13
<211> LENGTH: 15
<212> TYPE: PRT
<213> ORGANISM: Chlamydia trachomatis

<400> SEQUENCE: 13

Gln Leu Lys Gln Leu Gly Ala Leu Arg Gly Leu Met Ala Arg Lys
1               5                   10                  15

<210> SEQ ID NO 14
<211> LENGTH: 15
<212> TYPE: PRT
<213> ORGANISM: Mycoplasma pneumoniae

<400> SEQUENCE: 14

Asn Phe Thr Gln Leu Phe Gly Met Arg Gly Leu Met Ala Arg Lys
1               5                   10                  15

<210> SEQ ID NO 15
<211> LENGTH: 15
<212> TYPE: PRT
<213> ORGANISM: Bacillus subtilis

<400> SEQUENCE: 15

Asn Phe Thr Gln Leu Ala Gly Met Arg Gly Leu Met Ala Arg Lys
1               5                   10                  15

<210> SEQ ID NO 16
<211> LENGTH: 15
<212> TYPE: PRT
<213> ORGANISM: Staphylococcus aureus

<400> SEQUENCE: 16

Asn Phe Thr Gln Leu Ala Gly Met Arg Gly Leu Met Ala Arg Lys
```

```
<210> SEQ ID NO 17
<211> LENGTH: 15
<212> TYPE: PRT
<213> ORGANISM: Mycobacterium tuberculosis

<400> SEQUENCE: 17

Gln Thr Arg Thr Leu Ala Gly Met Lys Gly Leu Val Ala Arg Lys
1               5                   10                  15

<210> SEQ ID NO 18
<211> LENGTH: 15
<212> TYPE: PRT
<213> ORGANISM: Synechocystis sp

<400> SEQUENCE: 18

Gln Val Arg Gln Leu Val Gly Met Arg Gly Leu Met Ala Arg Lys
1               5                   10                  15

<210> SEQ ID NO 19
<211> LENGTH: 15
<212> TYPE: PRT
<213> ORGANISM: Aquifex aeolicus

<400> SEQUENCE: 19

Gln Ile Arg Gln Leu Ala Gly Met Arg Gly Leu Met Ala Arg Lys
1               5                   10                  15

<210> SEQ ID NO 20
<211> LENGTH: 15
<212> TYPE: PRT
<213> ORGANISM: Deinococcus radiodurans

<400> SEQUENCE: 20

Gln Ile Arg Gln Leu Ala Gly Met Arg Gly Leu Met Ala Arg Lys
1               5                   10                  15

<210> SEQ ID NO 21
<211> LENGTH: 15
<212> TYPE: PRT
<213> ORGANISM: Thermus thermophilus

<400> SEQUENCE: 21

Gln Ile Arg Gln Leu Cys Gly Leu Arg Gly Leu Met Ala Arg Lys
1               5                   10                  15

<210> SEQ ID NO 22
<211> LENGTH: 15
<212> TYPE: PRT
<213> ORGANISM: Thermus aquaticus

<400> SEQUENCE: 22

Gln Ile Arg Gln Leu Cys Gly Met Arg Gly Leu Met Ala Arg Lys
1               5                   10                  15

<210> SEQ ID NO 23
<211> LENGTH: 15
<212> TYPE: PRT
<213> ORGANISM: Human RNAP I

<400> SEQUENCE: 23

Asn Thr Met Gln Ile Ser Cys Leu Leu Gly Gln Ile Gly Arg Glu
1               5                   10                  15
```

```
<210> SEQ ID NO 24
<211> LENGTH: 15
<212> TYPE: PRT
<213> ORGANISM: Human RNAP II

<400> SEQUENCE: 24

Asn Ile Ser Gln Val Ile Ala Val Val Gly Gln Gln Gly Arg Glu
1               5                   10                  15

<210> SEQ ID NO 25
<211> LENGTH: 15
<212> TYPE: PRT
<213> ORGANISM: Human RNAP III

<400> SEQUENCE: 25

Asn Ile Ser Gln Met Ile Ala Cys Val Gly Gln Gln Gly Arg Glu
1               5                   10                  15

<210> SEQ ID NO 26
<211> LENGTH: 41
<212> TYPE: DNA
<213> ORGANISM: Artificial Sequence
<220> FEATURE:
<223> OTHER INFORMATION: oligonucleotide primer

<400> SEQUENCE: 26
ccgtgcaccg actctgcacc gtctgggtat ccaggcattt g                 41

<210> SEQ ID NO 27
<211> LENGTH: 69
<212> TYPE: DNA
<213> ORGANISM: Artificial sequence
<220> FEATURE:
<223> OTHER INFORMATION: oligonucleotide primer

<400> SEQUENCE: 27
gcaacaacat cctgtccccg gcgaacggcg aaccaatcat cgttccgtct caggacgttg    60
tactgggtc                                                            69

<210> SEQ ID NO 28
<211> LENGTH: 51
<212> TYPE: DNA
<213> ORGANISM: Artificial sequence
<220> FEATURE:
<223> OTHER INFORMATION: oligonucleotide primer

<400> SEQUENCE: 28
gtcaaccagg cgctgggtaa aaaagcaatc tccaaaatgc tgaacacctg c             51

<210> SEQ ID NO 29
<211> LENGTH: 85
<212> TYPE: DNA
<213> ORGANISM: Artificial sequence
<220> FEATURE:
<223> OTHER INFORMATION: oligonucleotide primer

<400> SEQUENCE: 29
cgggcgaacg ctacaacaaa gttatcgata tctgggctgc ggcgaacgat cgtgtatcca    60
aagcgatgat ggataacctg caaac                                          85

<210> SEQ ID NO 30
<211> LENGTH: 64
<212> TYPE: DNA
<213> ORGANISM: Artificial sequence
<220> FEATURE:
<223> OTHER INFORMATION: oligonucleotide primer
```

```
<400> SEQUENCE: 30
ctacatgatg gccgactccg gtgcgcgtgg ttctgcggca cagattcgtc agcttgctgg      60
tatg                                                                  64

<210> SEQ ID NO 31
<211> LENGTH: 60
<212> TYPE: DNA
<213> ORGANISM: Artificial sequence
<220> FEATURE:
<223> OTHER INFORMATION: oligonucleotide primer

<400> SEQUENCE: 31
cgtcagcttg ctggtatgcg tggtctgatg gcgaagccgg atggctccat catcgaaacg      60

<210> SEQ ID NO 32
<211> LENGTH: 68
<212> TYPE: DNA
<213> ORGANISM: Artificial sequence
<220> FEATURE:
<223> OTHER INFORMATION: oligonucleotide primer

<400> SEQUENCE: 32
gtacttcatc tccacccacg gtgctcgtaa aggtctggcg gataccgcac tgaaaactgc      60
gaactccg                                                              68

<210> SEQ ID NO 33
<211> LENGTH: 70
<212> TYPE: DNA
<213> ORGANISM: Artificial sequence
<220> FEATURE:
<223> OTHER INFORMATION: oligonucleotide primer

<400> SEQUENCE: 33
gtgttatcgc gggacagtcc atcggtgaac cgggtacaca gctgaccatg cgtacgttcc      60
acatcggtgg                                                            70

<210> SEQ ID NO 34
<211> LENGTH: 34
<212> TYPE: DNA
<213> ORGANISM: Artificial sequence
<220> FEATURE:
<223> OTHER INFORMATION: oligonucleotide primer

<400> SEQUENCE: 34
ccaaggacat caccggtggt ctgccgcgcg ttgc                                 34

<210> SEQ ID NO 35
<211> LENGTH: 50
<212> TYPE: DNA
<213> ORGANISM: Artificial sequence
<220> FEATURE:
<223> OTHER INFORMATION: oligonucleotide primer

<400> SEQUENCE: 35
cgaagtacag gacgtatacc gtgtgcaggg cgttaagatt aacgataaac                 50
```